United States Patent [19]

Angelsen et al.

[11] Patent Number: 4,848,354

[45] Date of Patent: Jul. 18, 1989

[54] METHOD AND APPARATUS FOR INVESTIGATING A CIRCULATORY SYSTEM IN LIVING BIOLOGICAL STRUCTURES

[75] Inventors: Bjørn A. J. Angelsen, Trondheim; Kjell Kristoffersen, Oslo, both of Norway

[73] Assignee: Vingmed A/S, Oslo, Norway

[21] Appl. No.: 170,045

[22] Filed: Mar. 11, 1988

Related U.S. Application Data

[63] Continuation of Ser. No. 889,302, Jul. 18, 1986, abandoned, which is a continuation of Ser. No. 603,511, Apr. 24, 1984, abandoned.

[30] Foreign Application Priority Data

May 13, 1983 [NO] Norway .................................. 831718

[51] Int. Cl.$^4$ ................................................ A61B 8/06
[52] U.S. Cl. ........................... 128/660.05; 128/661.09; 73/861.25
[58] Field of Search ........................ 128/660, 661, 663; 73/861.25

[56] References Cited

U.S. PATENT DOCUMENTS

| 4,106,346 | 8/1978 | Matzuk ................................. 128/660 |
| 4,111,055 | 9/1978 | Skidmore, III ...................... 128/661 |
| 4,141,347 | 2/1979 | Green et al. ......................... 128/663 |
| 4,182,173 | 1/1980 | Papadofrangakis et al. . |
| 4,205,687 | 6/1980 | White et al. ......................... 128/663 |
| 4,217,909 | 8/1980 | Papadofrangakis et al. . |
| 4,257,278 | 3/1981 | Papadofrangakis et al. ....... 128/663 |
| 4,265,126 | 5/1981 | Papadofrangakis et al. . |
| 4,313,444 | 2/1982 | Glenn . |
| 4,324,258 | 4/1982 | Huebscher et al. . |
| 4,407,293 | 10/1983 | Suarez, Jr. et al. ................. 128/663 |
| 4,417,584 | 11/1983 | Cathignol et al. .................. 128/663 |

FOREIGN PATENT DOCUMENTS

0014793A1 of 0000 European Pat. Off. .
0092841A of 0000 European Pat. Off. .
821245 4/1982 Norway .
2112937A of 0000 United Kingdom .

OTHER PUBLICATIONS

MacPherson et al, "Angioscan: A Spectrum Analyser for Use with Ultrasonic Doppler Velocimeters", Journal of Medical Eng. & Tech., vol. 5, No. 2, Mar. 1981, pp. 84–85.

*Primary Examiner*—Ruth S. Smith
*Attorney, Agent, or Firm*—Ladas & Parry

[57] ABSTRACT

Method and apparatus for generating a multidimensional map of blood velocities in the circulatory system of living species, using the Doppler effect of backscattered ultrasound from the blood, with real time presentation on a display device, with the ability to select small sample volumes in the flow map where the information can be presented as a function of time together with the moving multidimensional map in real time. There is transmitted a pulsed ultrasonic beam which is swept in two or more dimensions through the region of the biological structure which is to be investigated. The backscattered ultrasonic signal is sampled in a number of depth volumes along each beam direction of the transmitted ultrasonic pulses. For each depth and beam direction there is determined a velocity parameter of the blood flow by means of the Doppler principle, and the velocity parameters from the whole region investigated are read into an image memory. Therefrom they are read out repeatedly for coded presentation on the display screen. By synthesizing on the basis of the backscattered signal from one or more selected sample volumes in the region investigated, there is generated an estimate signal to substitute the missing Doppler signal in these sample volumes while there is measured in other directions, for determining the frequency spectrum of the signal or a frequency parameter thereof, for example maximum frequency, which is simultaneously displayed as a function of time. The main use of the invention is for medical diagnosis, in particular in hospitals.

13 Claims, 20 Drawing Sheets

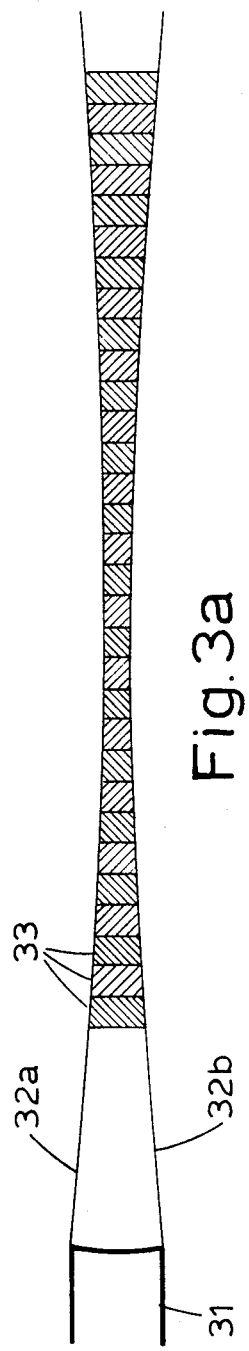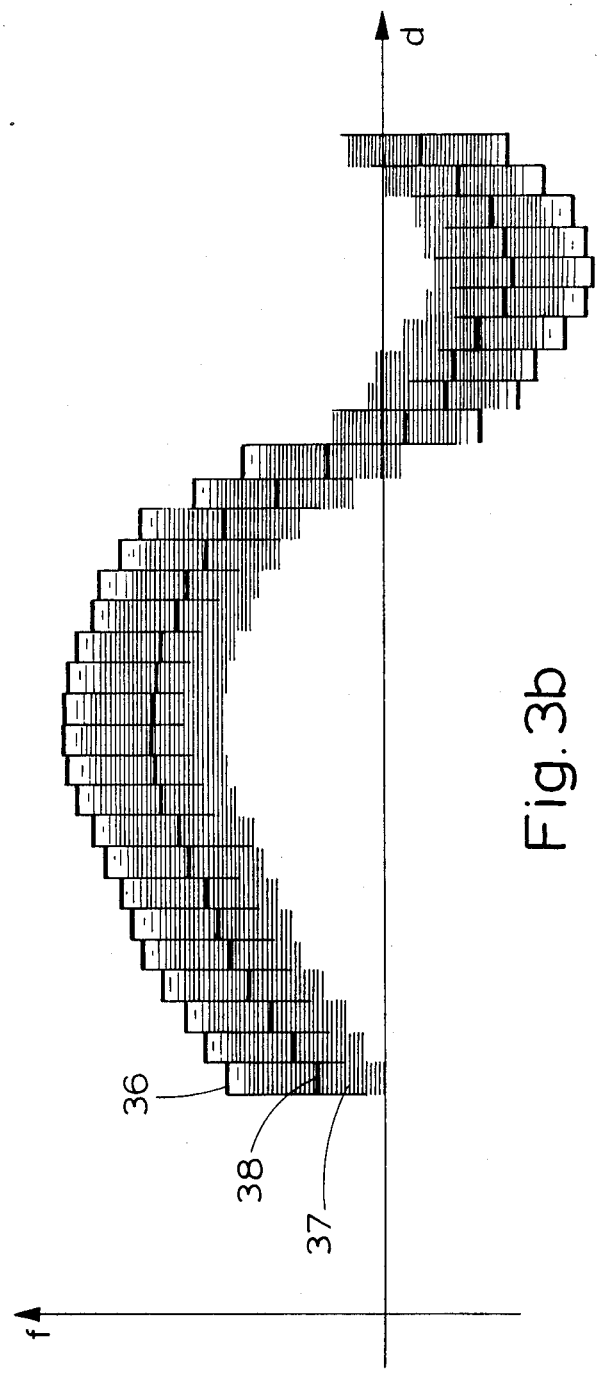

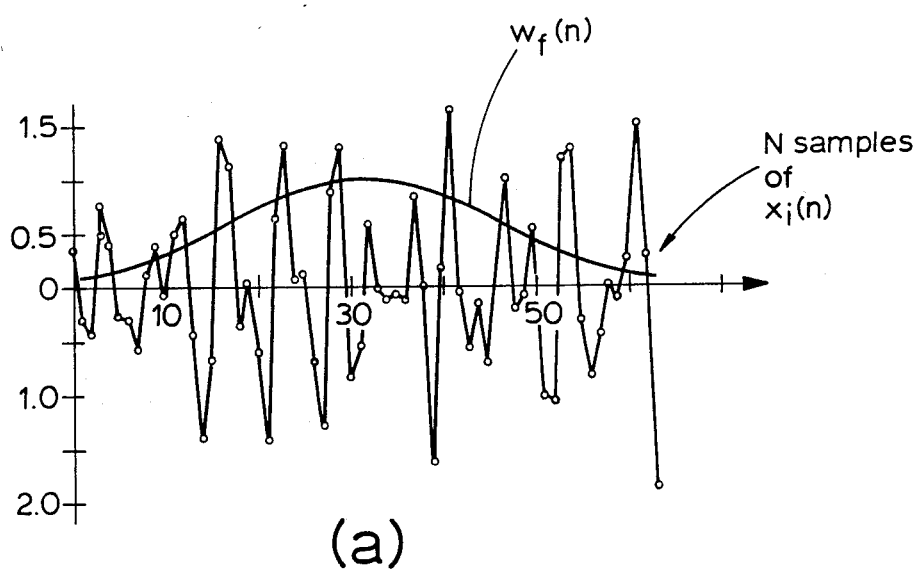
(a)
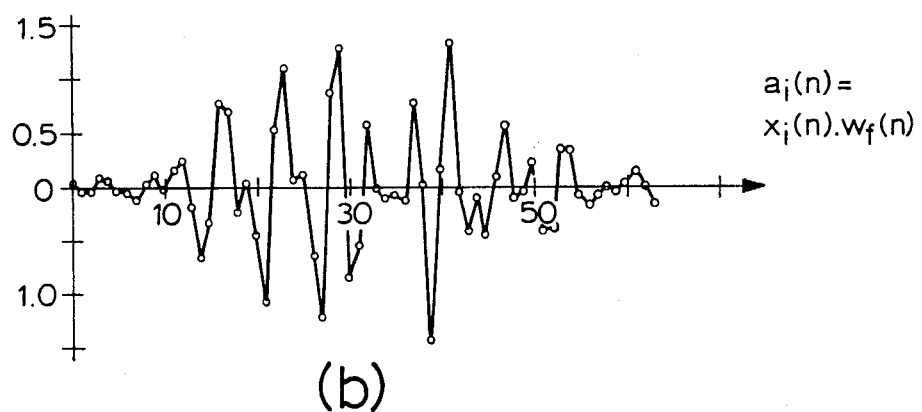
(b)
Fig. 15

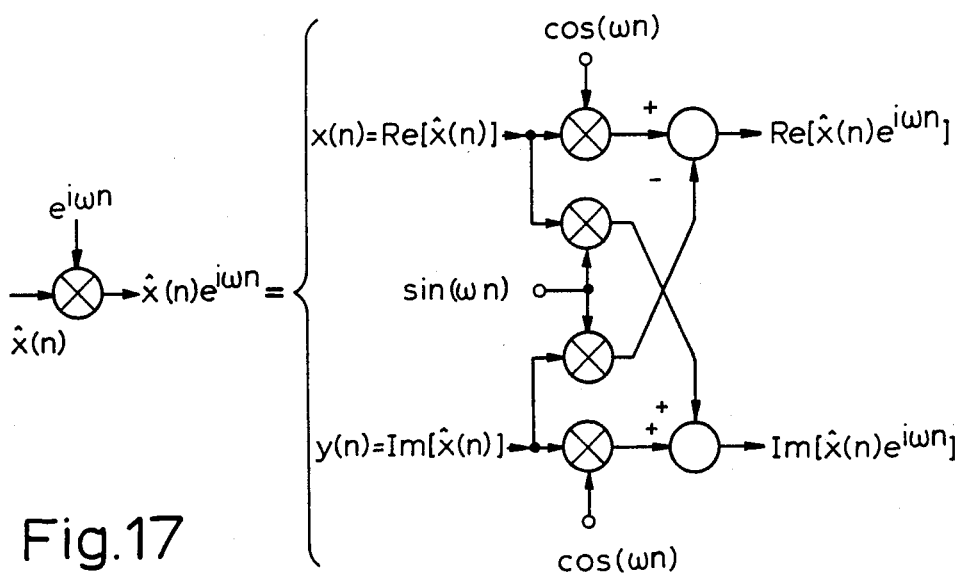
Fig.17
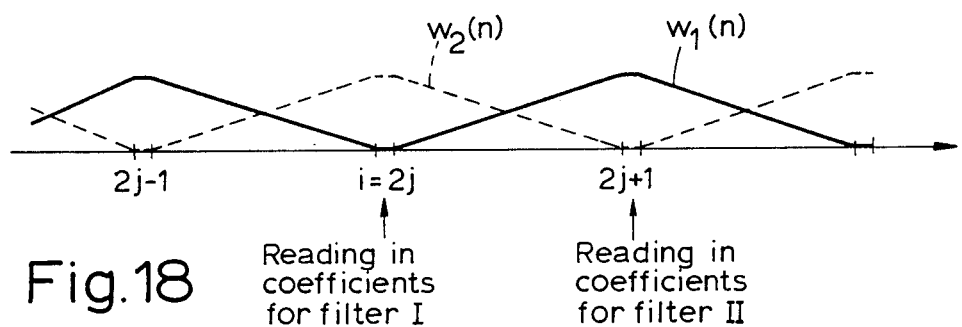
Fig.18
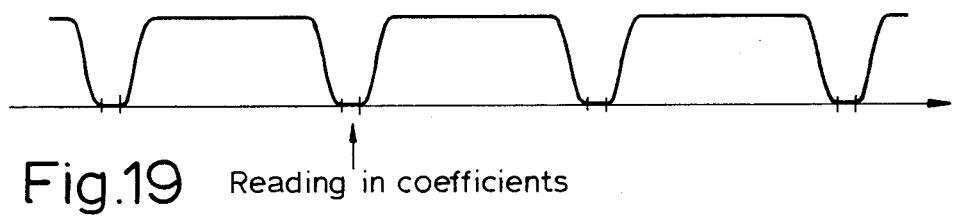
Fig.19 Reading in coefficients

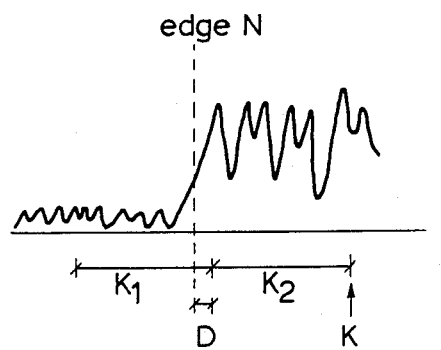 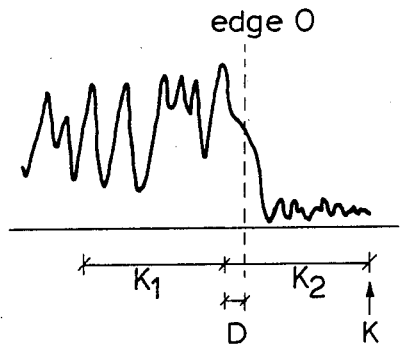
Fig. 29a        Fig. 29b
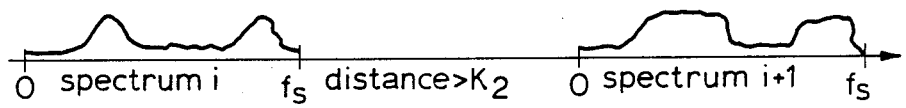
Fig. 30a
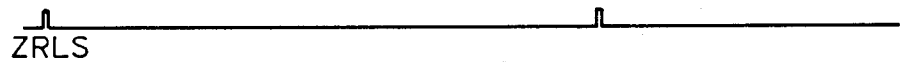
Fig. 30b

METHOD AND APPARATUS FOR INVESTIGATING A CIRCULATORY SYSTEM IN LIVING BIOLOGICAL STRUCTURES

This is a continuation of co-pending application Ser. No. 889,302 filed on July 18, 1986 which is a continuation of Ser. No. 603,511 filed Apr. 24, 1984, both now abandoned.

BACKGROUND OF THE INVENTION

This invention relates to a method and an apparatus for generating a multidimensional map of blood velocities in the circulatory system of living species, employing the Doppler shift of backscattered ultrasound from blood. The map is presented in real time on a display device, and the invention relates in particular to the possibility of selecting one or more sample volumes in the display from which the Doppler signal can be presented audibly through a loudspeaker or alike, and the frequency analysis of the Doppler signal can be presented as a function of time together with the moving flow map in real time, representing the time variation of the blood velocities in the sample volumes selected. The display of the blood velocities can also be presented together with a for practical purposes simultaneous image of tissue structures in the system, e.g. the heart muscle.

The field of the invention is ultrasound diagnosis of the cardiovascular system as being done in hospitals and the private physicians office.

There has both been presented scientific papers describing blood flow imaging, and commercial instruments that sweep the ultrasonic beam over a two dimensional field and calculate the Doppler shift as a function of depth to present a two dimensional color coded display of a blood velocity distribution. This invention differs from prior art in the ability to select one or more sample volumes in the displayed map from which one can get a continuous audible presentation of the Doppler signal and a display of the of the spectrum of the Doppler signal representing the blood velocities in the selected sample volumes versus time. The invention also differs from prior art in the method of high-pass filtering to remove backscattered signal from tissue structures, the method of calculating the Doppler shift, and the use of a continuously swept beam from a mechnically steerable transducer to generate the flow map.

The flow map is obtained by sweeping the ultrasonic beam to generate a time sequential measurement in different beam directions. The measurement in each sample volume is therefore intermittent, and to be able to give a continuous presentation of the Doppler signal from selected sample volumes, the invention uses a signal synthesizer which on the basis of short segments of the Doppler signal from a particular sample volume, generates a continuous substitute signal with spectral properties close to the original signal that would have been obtained from continuous measurements on that sample volume, and which can be presented in audible form and analysed instead of the original signal. By this an apparent continuous presentation of the signal from the sample volume can be presented although the measurement from this volume is done intermittently during short intervals with some distance in time.

In the interrupt intervals when measurements are not done in the particular sample volume, one can do Doppler measurements at other directions or one can also generate a pulse echo amplitude image of tissue structures using methods known per se, as can be seen in Norwegian patent application no. 82.1245 and U.S. Pat. No. 4,559,952. This type of time sharing between Doppler blood velocity measurements and pulse echo amplitude imaging allows for optimizing the shape of the transmitted pulse for the two types of measurements.

The interrupt intervals of the Doppler measurements for a particular sample volume are much larger than the correlation time of the Doppler signal. It is then difficult to estimate the true waveform of the missing Doppler signal. Instead one generates a substitute signal with approximately the same correlation properties (spectral properties) as the original signal, i.e. we are not concerned with the phase of the Fourier transform, only the amplitude.

Also we use the signal after the strong components from tissue structures have been removed by filtering, as a basis for the synthesis. This requires less relative accuracy in the estimation since the signal components from tissue structures are much stronger than the components from the blood. If we try to estimate the signal before the filtering, even a small relative error can give signal components comparable in magnitude to the components from blood and thus be very disturbing.

One should note that the Doppler measurements from different beam directions and the generation of the pulse echo amplitude image are done consecutively in time and are thus not truly simultaneous. However, the time interval to do all the measurements over the whole image field (both blood velocity and tissue image) can be made sufficiently short for the image to appear instantaneous on the screen with a frame rate of 10-20 images per sec. Thus for practical purposes a real time display can be obtained.

Although the invention relates to a multidimensional map of the blood flow, one will in most cases use a two dimensional map. The combined two-dimensional Doppler-amplitude image is presented on a suitable screen, for example a color video screen in which the echo amplitude image is for example coded in gray scale, whereas the Doppler image is produced as a color overlay as known per se. A proposal for a color code may be red for velocities towards the transducer and blue for velocities away from the transducer, with dark red and dark blue indicating low velocities, with transitions to light red/yellow and light blue/white for high velocities.

It is also important that the Doppler signal from the selected sample volumes may be presented in audible form, for example in headphones or a loudspeaker. The operator carrying out the investigation will to a large extent take advantage of the information contained in the audible signal. Therefore, it has much significance that the audibly presented Doppler signal is not substantially disturbed or distorted from what it is for a noninterrupted Doppler measurement.

The object of the invention is to provide a method and an apparatus which may quickly detect abnormalities of the blood flow in the heart and vessels. The investigation may be carried out by applying an ultrasonic transducer at the skin surface, thereby making the method noninvasive, in contrast to X-ray and radio isotope methods in which it is necessary to make injections in the body. The method may also be used in an invasive manner during operations, and the injection of an ultrasonic contrast liquid may also be employed in order to obtain a better Doppler image. In order to determine the absolute velocity of the blood in Doppler methods, there must be made corrections for the angle between the velocity vector of the scattering elements and the sound beam. By imaging the blood flow in a plane, the angle in this plane may be determined, and corrections of the velocity values for the angle in this plane can be made. By rotating the plane until a maximum velocity is obtained, the complete velocity vector will lie in the plane, and thereby the absolute velocity may be completely determined.

The present invention is based upon the use of a pulse type ultrasonic beam. In order to produce the above two-dimensional Doppler image the ultrasonic beam (1–20 MHz) is swept in several directions in a plane. For measurements on the heart this advantageously takes place with a sector sweeping of the beam, whereas a linear sweep or a combination of linear and sector sweeping may be preferable when measurements on pheripheral vessels, abdominal organs and fetuses are made.

In the claims there are set forth closer statements of the method and the apparatus according to the invention.

BRIEF DESCRIPTION OF THE DRAWINGS

In the following description with reference to the drawings, various aspects of the invention shall be more closely explained, including additional specific and unique solutions which are advantageous in the practical implementation of the invention.

FIG. 3b shows in relation to FIG. 3a the Doppler frequency spectra at different depths along the ultrasonic beam, FIG. 4 serves to illustrate certain geometrical relationships with respect to a continuously swept (rotated) transducer, FIG. 17 illustrates the splitting of a complex multiplication which is included in the block diagram of FIG. 16, into real operations, FIG. 18 shows examples of weighting functions for the mixing of signals from two filters as shown in FIG. 16, FIG. 19 shows an example of a weighting function when one filter in the block diagram of FIG. 16 is used.

DESCRIPTION OF THE PREFERRED EMBODIMENTS

The system as a whole

Figure 1:
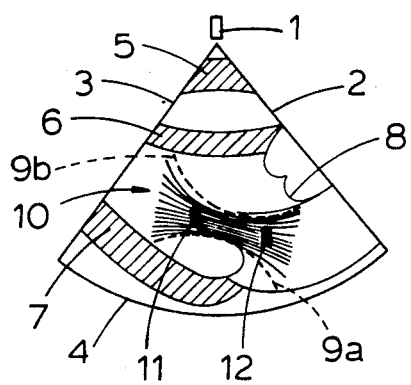
FIG. 1 shows an example of a sector image of a biological structure, including a two-dimensional blood velocity field and an indication of two selected points for presentation of the frequency spectra.

In FIG. 1 there is schematically shown a longitudinal cut through the heart and a transducer 1, which may possibly be a transducer arrangement or array consisting of several transducer elements, and which by means of a swept ultrasonic beam covers a plane, sector-shaped region of a biological structure delimited by straight lines 2 and 3 and a circular arc 4. The simplified picture shown comprises cardiac muscle tissue with comparatively high ultrasonic reflectivity 5, 6, 7 and 8, and a portion of blood flow 10 bounded by the interrupted lines 9a and 9b. The blood flow 10 is marked with "flow lines", whereby the density of these lines is meant to illustrate the blood flow velocity in the various points of the blood flow. There are specifically indicated two points or regions 11 and 12 which may be subjected to particular investigations or measurements, as will appear from the following description. Other formats with different sweeping of the beam, for example a linear sweep, may also be employed.

Thus, FIG. 1 shows a presentation in which an echo amplitude image of the biological structure is combined with an imaging of the blood flow velocity field in a two-dimensional display. The velocity dirtibution in the blood flow 10 can thus be shown in a coded form, for example with a grey scale or with a color scale. The surrounding biological structure is imaged by means of the echo amplitude method by coding in a grey scale or in colors.

FIG. 2 shows a representation (a and b) of curves relating to measured Doppler frequencies as a function of time in two points or regions, for example as indicated at 11 or 12 in FIG. 1. The presentation of the Doppler spectrum as a function of time in such a definite point is highly significant when investigating a circulatory system, and it is an important aspect of the present invention that this presentation of the Doppler frequencies may for practical purposes take place simultaneously with the two dimensional information which is apparent from FIG. 1. The Doppler frequencies shown as a function of time may either be displayed on the same screen as the combined image according to FIG. 1, or on a separate screen.

Figure 2A:
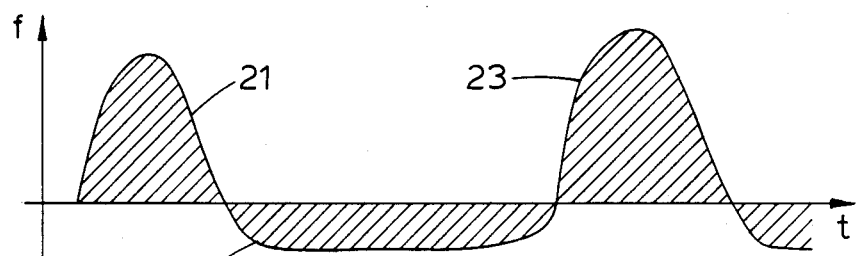
FIG. 2a and FIG. 2b show an example of producing Doppler spectra from two points as a function of time, FIG. 3a schematically shows a transducer with an ultrasonic beam emitted therefrom.
Figure 2B:
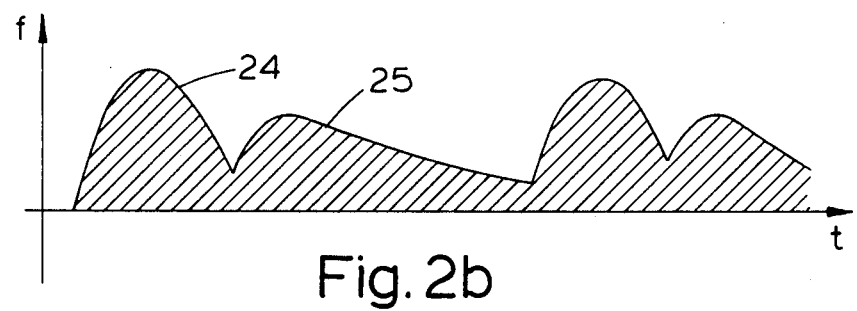

FIG. 2a shows a typical curve having two peaks 21 and 23 which represent high positive Doppler frequencies, i.e. high blood flow velocities in a direction towards the transducer, whereas the negative frequencies in curve portion 22 represent blood flow velocities in a direction away from the transducer. In FIG. 2b the complete frequency spectrum and therefore all blood flow velocities are in the positive region, i.e. all blood flow velocities are all the time directed toward the transducer. According to FIG. 2 the blood velocity curves at two points are simultaneously presented as a function of time. The presentation or display may of course relate only to one point or to more than two points.

FIG. 3a shows an example of how an ultrasonic beam may be shaped from a transducer 31 which may for example be used in an arrangement for sector sweeping with an image presentation as in FIG. 1. The ultrasonic beam in FIG. 3a is delimited by lines 32a and 32b, which shows that the beam initially has a portion with a decreasing cross-section seen in the beam direction or depth, and thereafter again diverges. The ultrasonic beam is shown with a subdivision into smaller regions 33, each of which represents a depth point or sample volume in the structure to be investigated. In the example of FIG. 3a there is shown a number of thirty one sample volumes 33.

For each beam direction a certain time is needed to provide pulse transmissions and measurement of the backscattered signal, for example $T_r \ldots 3$ ms. The backscattered signal from each depth (sample volume) is sampled and processed for determining the blood flow velocity. Since the sound beam has a certain width and the transmitted pulse has a certain length, only a limited spatial resolution is obtained. Each depth sample then contains information regarding the velocity in a certain region, namely the above sample volume. This region contains scatterers having different velocities and the scatterers are present in the region during a limited time. Therefore there will appear a spectrum of Doppler shifted frequencies as indicated in FIG. 3b. FIG. 3b shows Doppler frequencies as a function of depth, associated with the ultrasonic beam of FIG. 3a, which is subdivided into sample volumes 33 as mentioned above. For each of these points the frequency spectrum is shown in the form of a gray scale 37 in which the brightening indicates larger or smaller contents of the different frequencies in the point or region concerned. In each region the maximum absolute velocity will give the most interesting information regarding the blood flow. Therefore, it is desirable to find this maximum velocity as a function of depth along the beam. In FIG. 3b this is illustrated as bold lines around the envelope of the spectrum. The mean velocity as a function of depth is indicated as the bold lines in the middle of the spectrum.

A closer description of a particular solution for determining the maximum blood flow velocities from a measured Doppler spectrum in each point or sample volume, will follow later with reference to FIGS. 23-33 of the drawings.

For each direction the maximum Doppler shift will be determined at a number of L depths, for example $L=31$ in FIGS. 3a and 3b. The two-dimensional Doppler picture (FIG. 1) is then built up from the set of the maximum velocities (positive and negative) at the L depths for N beam directions obtained by the sweeping of the beam. For each direction only the radial velocity component of the scattering elements along the sound beam, is measured. By imaging the blood flow in two dimensions the angle in the plane between the blood velocity direction and the sound beam may be determined. The velocity values may thereby be corrected with respect to the angle as described above.

The detection of the maximum velocity is more sensitive to noise than detection of the mean velocity in the sample volume. With a low signal-to-noise ratio it may therefore be advantageous to utilize the mean velocity instead of the maximum velocity for the imaging. The spectrum bandwidth may also be of interest for certain applications, in particular when combined with the mean velocity to approximate the maximum velocityas the sum of the mean velocity and half the bandwidth.

The sound beam may either be moved continuously, or step-wise so that it will be at rest during the measurement in each direction and is moved step-wise between the directions.

Figure 4:
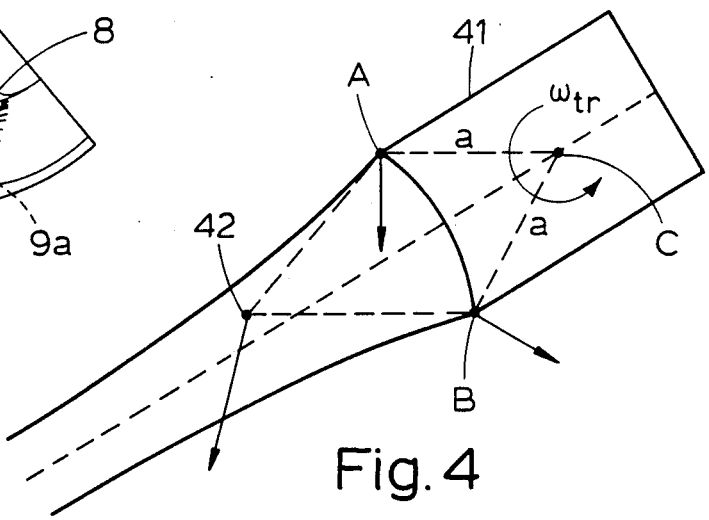

By continuous movement of the sound beam different parts of the transducer surface will move with different velocities with respect to the scattering element. This is illustrated in FIG. 4 in the case of sector sweeping, in which point A, because of the movement of the transducer, has an additional velocity towards the scatterer 42, whereas point B has an additional velocity away from the scatterer. Over the transducer surface the different points at that surface will have additional velocities varying continuously between point A and point B. The continuous movement of the transducer 41 therefore results in a broadening of the Doppler shift from the scattering element 42.

Equivalently, the total sound field may be considered to be composed of contributions from the various points on the transducer surface, by superposition. Each point has a spherical radiation pattern; however, because of interference between the various points, the directive beam from the transducer will result. When the transducer is rotated, a scattering element will initially enter the radiation field and then, after a certain time, leave it. The signal from the scatterer will then be amplitude and phase modulated because of the sound field variations. This causes a broadening of the Doppler shift from the scatterer. This broadening is equivalent to the broadening resulting from the varying velocity between the scatterer and the points on the transducer surface, caused by rotation of the transducer.

The time $T_r$ during which the measurement for each direction is carried out, should be made equal to the time during which the scatterers are observed in the focal zone of the beam. Assume that the image is built up by N beam directions. The time $T_{db}$ it takes to build up a Doppler image with a continuous movement of the sound beam will be $$T_{db} = NT_r \qquad (1)$$

Let d be the beam diameter at the focal zone and f the focal length. By a sector sweep of the beam, each beam direction should cover an aperture angle in the image of $$\Delta\Phi = d/f \qquad (2)$$

When the transducer is rotated continuously, it is then preferable to choose a rotational velocity of $$\omega_{tr} = \Delta\Phi/T_r \qquad (3)$$

The aperture angle of the image will then be $$\Phi_{db} = \omega_{tr}T_{db} = Nd/f \qquad (4)$$

The maximum additive velocity relative to a scatterer for a point on the transducer face, is due to the rotation according to FIG. 4 (with a being the distance from the rotational center C to point A and point B, respectively):

$$\Delta v = \omega_{tr}a \qquad (5)$$

When the sound beam is moved step-wise, there will be a discontinuity in the received signal each time the sound beam is moved. In order to remove reflections from tissue, the Doppler instrument high-pass filter requires a transient time $T_{HP}$, before the signal may be utilized for an analysis of the blood velocity. The time used for taking one Doppler image with a step-wise movement of the sound beam, will therefore be:

$$T_{db} = N(T_r + T_{HP}) \qquad (6)$$

The transient time of the high-pass filter is lost time and accordingly, a continuously movable sound beam is preferable.

When the Doppler image of the blood velocity distribution has been formed, there may be carried out a new sweep of the sound beam for generating an echo amplitude image. For this picture there may be used a shorter transmitted pulse than the the Doppler measurement in order to obtain a better longitudinal resolution. During Doppler measurement a lower resolution is permitted, in order to improve the signal-to-noise ratio. For optimizing the amplitude and the Doppler image separately it may be an advantage to employ different transducers for these two modes. A broad-band transducer is used for the echo amplitude image and a highly sensitive transducer for the Doppler image, for which it is common practice to trade bandwidth for sensitivity.

For the echo amplitude imaging there is only employed one pulse for each beam direction. The time $T_{ab}$ it takes to form one echo amplitude image will therefore become shorter than the time it takes to generate a Doppler image. The total picture frame time for the Doppler and the echo image will therefore be:

$$T_{br} = T_{db} + T_{ab} + (T_{HP}) \qquad (7)$$

$T_{HP}$ in parenthesis is only involved with a continuous movement of the transducer after the forming of the echo amplitude image, and the forming of the two-dimensional blood velocity Doppler image is commenced. Thereby the Doppler spectrum at a point will be sampled at a frequency $$f_{br} = 1/T_{br} \qquad (8)$$

Figure 5:
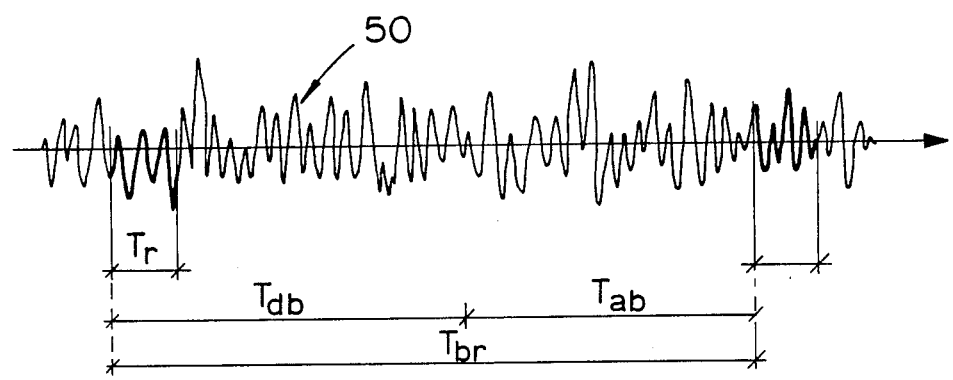
FIG. 5 shows an example of a Doppler signal as a function of time, and time slots for a single sample volume.

The time distribution is schematically shown in FIG. 5, in which reference numeral 50 designates the Doppler signal that would have been obtained with a continuous measurement on the sample volume.

Typical figures for a practical embodiment are:

| | | |
|---|---|---|
| N = 20 | $T_r$ = 3 ms | $T_{ab}$ = 15 ms |
| d = 3 mm | f = 70 mm | a = 10 mm | which give

| | |
|---|---|
| = 2,46° | |
| tr = 0.82 degrees/ms | |
| db = 49° | |
| v = 14.3 cm/s | |
| $T_{db}$ = 60 ms | |
| $T_{br}$ = 75 ms | $f_{br}$ = 13.3 Hz |

The additional velocity $\Delta v$ is the maximum value which may occur. This only occurs when the scattering element lies on the straight line indicating the direction of v, through point A or B in FIG. 4. Otherwise there will be an additional velocity given by the component of $\Delta v$ along the line from the scattering element to point A or B. For a scattering element on the transducer axis at a distance of 70 mm this angle may be 40°. This gives $\Delta v \cos 40 \approx 10$ cm/s. Since the scattering element velocity is often 1 m/s or more (as much as 6 m/s), this velocity error may be neglected for most purposes.

During the time $T_{br}$ the velocity may change much, and for presenting the Doppler frequencies as a function of time (FIG. 2) it is an advantage to provide for an interpolation between the samples. Moreover, there only exists segments of the Doppler signal, having a length $T_r$ and a time separation of $T_{br}$ for each sample volume as illustrated in FIG. 5. It is of interest to listen to the Doppler signal in selected points. For this purpose there is employed a synthesizer which on the basis of segments of the Doppler signal, synthesizes a continuous substitute signal which is similar to the original Doppler signal as hypothetically obtained by continuous Doppler measurements on the sample volume. By frequency analysis of the synthesized signal there is provided a interpolated spectrum to be presented as a function of time.

Figure 6:
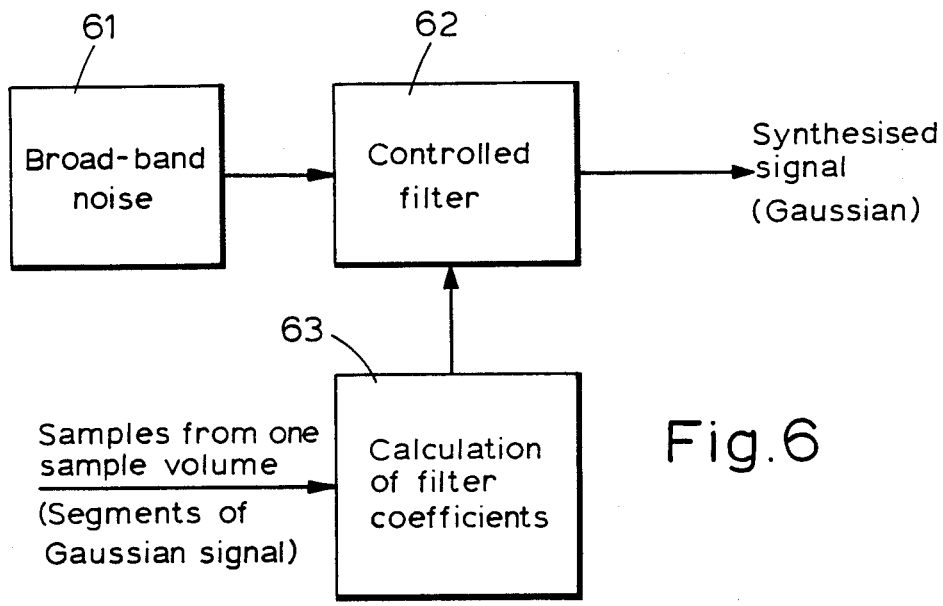
FIG. 6 shows a block diagram of a signal synthesizer.

A block diagram of a synthesizer for the signal from one depth is shown in FIG. 6. A broad-band (approximately white) excitation signal, for example noise from a generator 61, is applied to a filter 62, the transfer function of which may be controlled. If the noise is of the Gaussian type, the output of the filter 62 will be a Gaussian signal having a spectrum given by the transfer function of the filter. Because of the band pass function of the filter there may also be used a non-Gaussian signal, for example binary noise or a deterministic pulse train. The filter output will then be approximately Gaussian. Since the Doppler signal is Gaussian also, the synthesized signal will be of the same type as the Doppler signal. By controlling the filter coefficients, there is obtained an approximation to the real spectrum of the Doppler signal. Segments of the Doppler signal which stem from one sample volume, are then used in a calculating unit 63 for determining the filter coefficients as a function of time. An example showing the calculation of the filter coefficients is described more closely below with reference to FIGS. 13-19 of the drawings.

Figure 7:
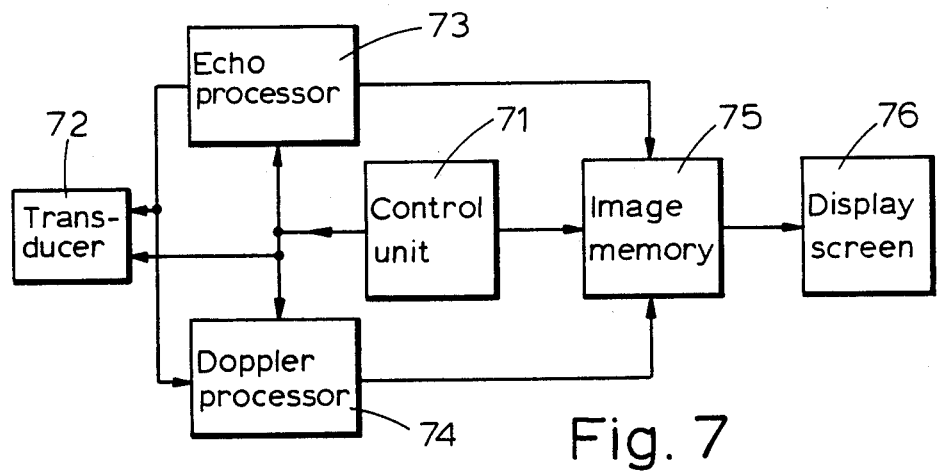
FIG. 7 shows a simplified block diagram of a complete apparatus according to the invention.

FIG. 7 shows a block diagram of a complete apparatus according to the invention, for carrying out the method described. A control unit 71 controls a sound beam from a transducer unit 72. This unit is successively connected to an echo amplitude processor 73 and a Doppler processor 74. The echo amplitude processor 73 gives the amplitude of backscattered sound from a short pulse for a given direction of the sound beam. This is read into an image memory 75 in a corresponding direction. The Doppler processor 74 determines the maximum (or for example the mean) Doppler shift as a function of the depth for each beam direction. This is also read into the image memory 75 in a corresponding direction. The image memory 75 is then read out horizontally for a combined presentation of the echo amplitude image and the blood flow velocity image on a display screen 76.

The Doppler processor

A. General description

Figure 8:
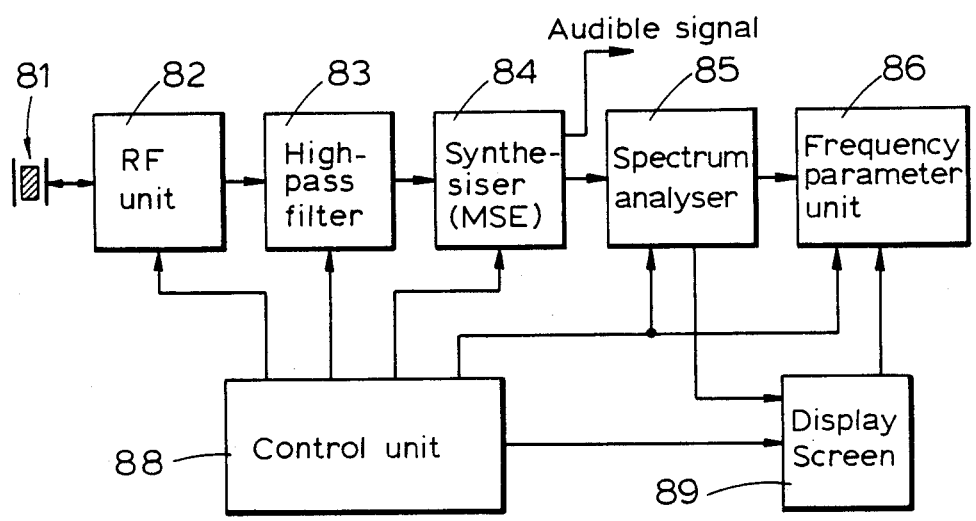
FIG. 8 shows a block diagram of a Doppler processor with an associated transducer and display screen, in particular for displaying a radial blood flow velocity field in one dimension (depth) along an ultrasonic beam.

The components of a Doppler processor which may be included in tha apparatus of FIG. 7, shall be discussed in the following description with reference to FIG. 8. This figure shows a transducer unit 81 which may for example be similar to the transducer 1 in FIG. 1 or the unit 72 in FIG. 7, and, moreover, a RF-unit 82 which is a required transmitter-receiver assembly for high frequency electrical signals to and from unit 81, as well as a high-pass filter 83, an estimator or synthesizer 84, a spectrum analyzer 85 and a frequency parameter unit 86. These units are controlled from a control unit 88 which may be considered as included in control unit 71 in FIG. 7. Finally, FIG. 8 shows a display screen 89 which may correspond to the image memory 75 and the screen 76 in FIG. 7. The arrangement of FIG. 8 is illustrated in a form which mages possible an explanation of the necessary functions for determining the frequency spectrum and parameters without referring back to FIG. 7. These functions with associated units and circuits besides will be discussed more closely by means of a number of the following figures of the drawings.

The present invention involves a serial signal processing in the Doppler processor, i.e. the same processing unit is used for analysis of all N depths in series, in contrast to parallel processing where a separate signal processing unit is used for each depth. Parallel processing can be used but involves a larger volume of electronics.

In serial signal processing a filter unit carries out high-pass filtering with respect to all depths as the signal arrives. This requires storing of the signal and the methods having been presented hitherto, employ digital storage. With present technology this imposes a limitation in the dynamic range of the signal. The present invention employs analog storage in a specific manner so that such limitation of the dynamic range does not arise.

Because of the width of the sound beam and the length of the transmitted pulse, the spatial resolution will be limited. This means that each depth sample contains a spectrum of Doppler frequencies. The methods which have been used in the serial signal processing for multi-depth measurements, have calculated a form of mean Doppler shift for each depth. Accordingly, it has not been possible to measure the maximum velocities. The present method carries out a full spectrum analysis at all depths and on this basis there is extracted a frequency which corresponds to the maximum velocity in each sample volume.

The operation of the arrangement in FIG. 8 shall be explained with reference also to the signal curves shown in FIG. 9. Control unit 88 delivers time sequential control signals to the other units in FIG. 8. It generates inter alia RF-pulses at intervals $T_s$ as shown at the top (a) of FIG. 9. These pulses energize the transducer 81 which generates acoustic pulses. The same transducer picks up a backscattered signal (b) which is amplified in RF-unit 82. By mixing according to known methods in the RF-unit the quadrature components, $x_n(t)$ and $y_n(t)$, of the received signal, are derived, see curves at (c) and (d) in FIG. 9. These components are best defined mathematically. Let the received RF-signal from pulse n be $$e_n(t) = Re\{\hat{x}_n(t)e^{i\omega_0 t}\} \tag{9}$$

in which t is time running from the pulse transmission and $\omega_0$ is the FR angular frequency of the transmitted pulse. $x_n(t)$ is the complex envelope of the signal and is given as $$\hat{x}_n(t) = x_n(t) + y_n(t) \tag{10}$$

in which $i = \sqrt{-1}$ is the imaginary unit. This defines $$x_n(t) = Re(\hat{x}_n(t) \text{ and } y_n(t) = Im(\hat{x}_n(t)) \tag{11}$$

Figure 9:
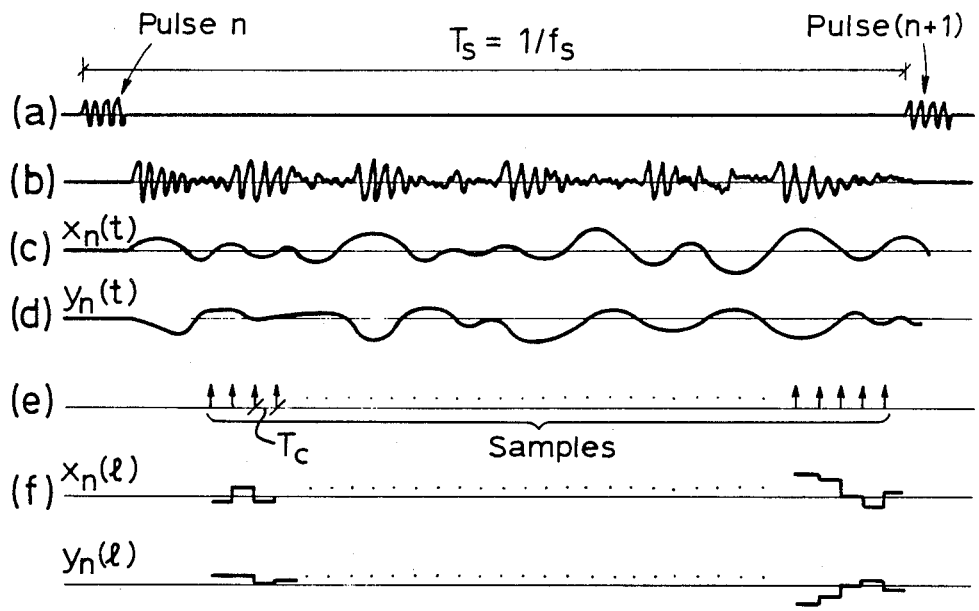
FIG. 9 shows typical signals which are found in the Doppler processor of FIG. 8.

$x_n$ and $y_n$ are subjected to filtering according to principles known for example from radar and sonar (such as a signal adapted filter) before sampling which is controlled by the sample control signal (e, FIG. 9). This gives the signals $x_n$ (l) and $y_n$ (l) as shown at (f) and (g) in FIG. 9, where $l = 1, \ldots, L$ designates the numbering of the depths. The high-pass filter unit 83 operates in synchronism on these signals in order to remove reflections from tissue.

B. The high-pass filter

Figure 10:
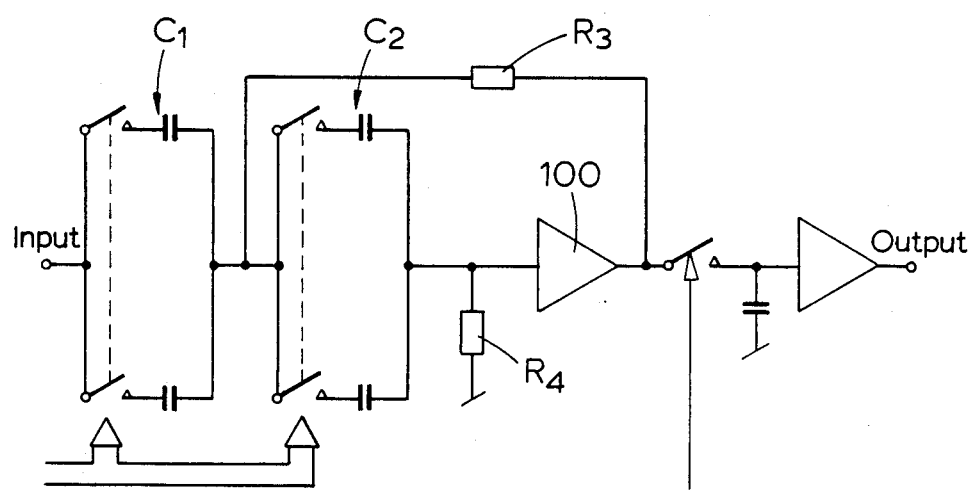
FIG. 10 shows a high-pass filter unit which is included in the Doppler processor of FIG. 8.
Figure 11:
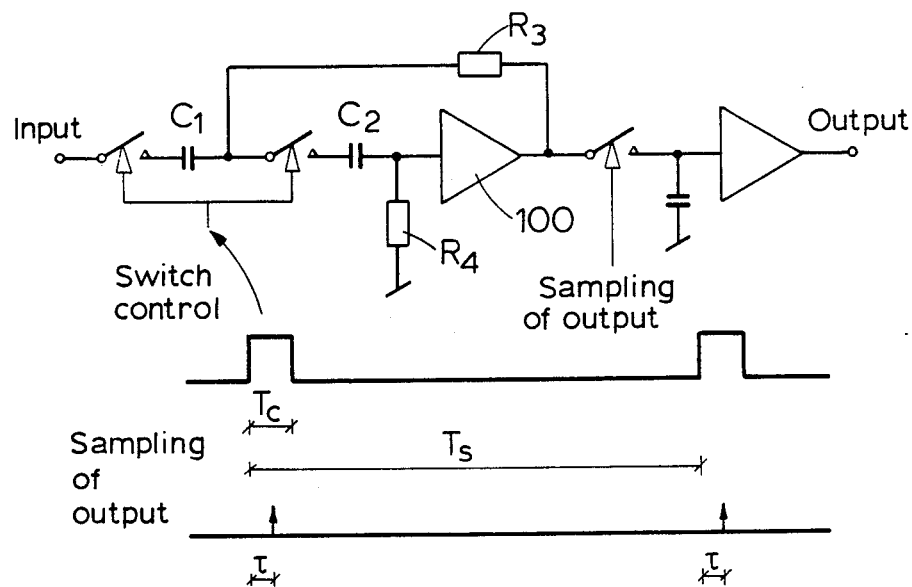
FIG. 11 shows the function of the high-pass filter unit of FIG. 10, with respect to one depth along the ultrasonic beam.

The fundamental principle of a two-pole high-pass filter unit which may form the high-pass filter 83, is shown in more detail in FIG. 10. The unit consists of two capacitor banks $C_1$ and $C_2$. The capacitors are switched on sequentially by multiplexers controlled by depth addresses. The switching on time for a capacitor group with respect to one depth, is $T_c$. Reference numeral 100 designates an amplifier and $R_3$ and $R_4$ are resistors. When two capacitors for one depth are connected, the system operates as a multiple feedback active high-pass filter for this depth. While the filter operates on other depths, the capacitors for this depth are disconnected and maintain their charges until they are again switched on for this depth after the next transmitted pulse. The output is sampled and held with a delay $\tau$ after switching-on a capacitor group. The delay $\tau$ serves to improve the transfer function of the filter. The function of the filter for each depth is additionally described with reference to FIG. 11. The capacitors are switched on during a time $T_c$ at intervals $T_s$.

Figure 12:
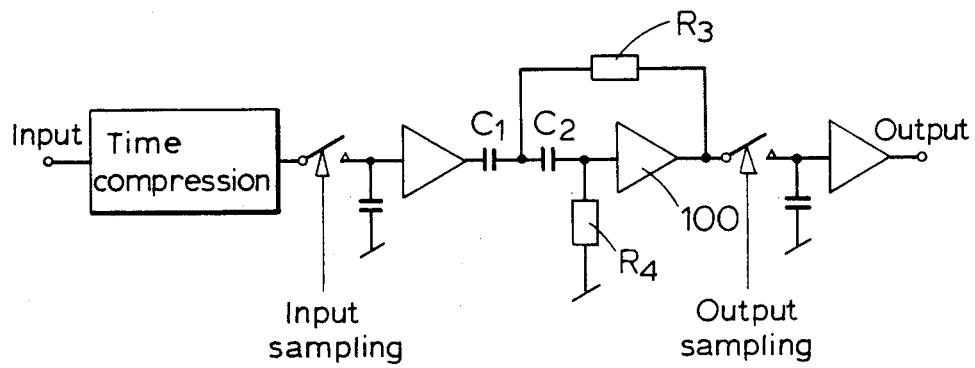
FIG. 12 shows a simplified diagram for additional explanation of the function of the high-pass filter unit of FIG. 10, with respect to one depth.

The filter is working during the period $T_c$ in which the control signal is high. During the remaining part of the period the capacitor charges do not change. Therefore, the filter function may be described by the diagram in FIG. 12.

Since the filter does not observe what takes place with the input signal when the switches are open, there may be carried out a time compression by a factor $T_c/T_s$ at the input. The filter will then perform as a continuous filter with a sample-and-hold circuit on the input and with sampling of the output. If the cut-off frequency of the continuous filter is $f_{oc}$, the cut-off frequency without time compression for the sampled system will be $$f_o = \frac{T_c}{T_s} f_{oc} \tag{12}$$

The Q factor of the filter is not changed by the time compression. In order to get two zero crossings in the frequency response for $\omega = 0$, the value of $\tau$ must be chosen equal to $$\tau = \frac{1}{\omega_{oc}} \left[ \tan^{-1}\left( \frac{e^{\tau \zeta \omega_{oc} T_c} - \cos \omega_{oc} T_c}{\sin \omega_{oc} T_c} \right) - \sin^{-1} \zeta \right] \tag{13}$$

$$\omega_{oc} = 2\pi f_{oc} = \frac{1}{\sqrt{R_3 R_4 C_1 C_2}}$$

$$\omega_{oc} = \sqrt{1 - \zeta^2}\, \omega_{oc}$$

$$\zeta = \frac{1}{2Q} = \frac{\omega_{oc}}{2} [R_4(C_1 + C_2) - R_3 C_2(A - 1)]$$

A is the gain of the filter amplifier.

Several two-pole filter sections may be connected in cascade to obtain a higher order response. It is then not necessary to carry out sampling of the signal between each section. So as to reduce the effect of switching transients it may be an advantage to provide for intermediate sampling of the signal after a certain number of two-pole sections, for example after 4 poles. It must then be provided for a corresponding delay between the switching-on of the capacitors and sampling on the output as described above.

C. The Doppler signal synthesizer

After high-pass filtering as just described, there follows in FIG. 8 a synthesizer 84 which in general is adapted to synthesize a stationary Gaussian signal from segments of another presented Gaussian signal so that the stochastic properties of the synthesized signal given by the autocorrelation function, approximate the stochastic properties of the present signal. As in the present case the method may be employed with advantage by blood flow measurements based upon the Doppler effect for backscattered ultrasound from blood. The Doppler signal will be a Gaussian signal and with regular interruptions in the Doppler measurement for short intervals, there will be a need for replacement of this directly measured Doppler signal by an estimated signal, either all the time or during portions of the time.

The synthesized signal derived by the method to be described below, may be utilized as an estimate on the basis of segments of the directly measured signal.

Figure 13:
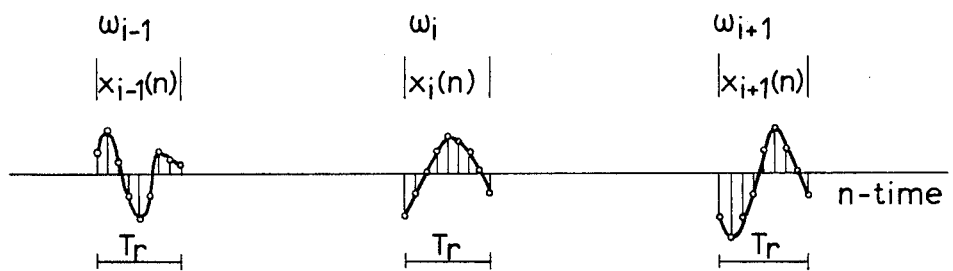
FIG. 13 illustrates examples of sections of segments of the Doppler signal as presented at the output from the high-pass filter.

It is assumed that there are presented segments of the Doppler signal with a length $T_r$ from the sample volume selected, from the output of the high-pass filter, at regular intervals as shown in FIG. 13. These segments are used for calculating the coefficients in a filter which is supplied with broad-hand (approximately white) noise or another suitable excitation, for example a pulse train. The output of this filter will then be approximately Gaussian, and this is employed as the synthetic signal. The main structure of the synthesizer is illustrated in the above FIG. 6.

The stochastic properties of a non-stationary Gaussian signal is described by the autocorrelation function of the signal $R(t_1, t_2)$. If the signal is stationary, this will be a function of $t_2 - t_1$. There may then be defined a power spectrum for the signal as the Fourier transform of the autocorrelation function.

For non-stationary signals there may be calculated a short time spectrum over such a short time that the signal is substantially stationary. Short time spectra for various sample functions of the same process ensemble and in the same time interval will be somewhat different because of the stochastic uncertainly in the spectral estimation. There may be carried out an ensemble averaging over all short time spectra and this will give the velocity distribution in the sample volume convolved with the spectral window employed and the transit time window of the blood through the sample volume.

Figure 14:
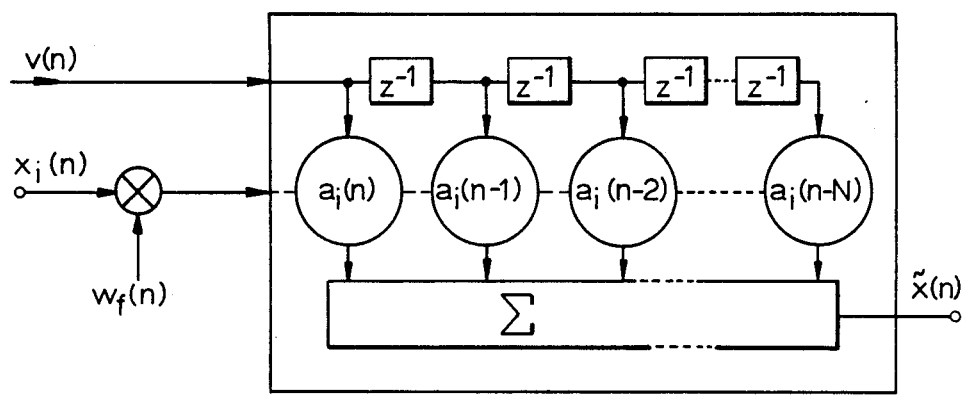
FIG. 14 is a block diagram of a synthesizer havinga transversal filter for the synthesis of a stationary signal from segments as shown for example in FIG. 13, FIGS. 15a and b illustrate the multiplication of a given signal with a weighting function for generating filter coefficients to be used in the filter of FIG. 14.

It is first described how a stationary Gaussian signal with substantially the same power spectrum as another given stationary Gaussian signal may be synthesized, from a segment of this given signal. The block diagram of a synthesizer which does this is shown in FIG. 14 for a real signal. N samples of the signal are weighted with a weighting function $w_f(n)$ thereby obtaining the coefficients $$a_i(n) = x_i(n) w_f(n) \tag{14}$$

This is illustrated in FIGS. 15a and b. The weighting function is of the same type as used in the spectral estimation in order to reduce the sidelobe level and may for example be a Hamming or Hanning window. It is used here to reduce the side lobe level in the spectrum of the synthesized signal.

The coefficients $a_i(n)$ are utilized in a transversal filter which is supplied with broad-band (approximately white) noise $v(n)$, as shown in FIG. 14. The synthesized signal is $\bar{x}(n)$. Storage and delay of the signal by one step of n is indicated by $z^{-1}$. The drive signal $v(n)$ may be broad-band (approximately white) Gaussian noise, but there may also be used broad-band binary noise or similar wideband sources if the filter has many coefficients as described above. In view of the Central-Limit- Theorem $\bar{x}(n)$ will then be approximately Gaussian. The binary noise has the advantage that in the filter one will only have multiplication with $\pm 1$, and the delays may be provided for by data flip-flops or digital shift registers. The power spectrum of the synthesized signal is $$G_{\bar{x}\bar{x}}(\omega)=1/N|F\{w_f(n)x_i(n)\}|2 \approx G_{xx}*|W_f|2.N \qquad (15)$$

in which F( ) indicates the Fourier transform, $W_f$( ) is the Fourier transform of $w_f$, $G_{\bar{x}\bar{x}}$ is the power spectrum of $\bar{x}$ and * indicates convolution in the frequency plane. The coefficients given above may also be changed through certain types of linear transforms (all-pass operation) without changing the power spectrum of the synthesized signal. This may have the advantage that the impulse response of the filter is made symmetric so that the number of multiplications is reduced to the half number, but it has also the disadvantage that there must be performed a linear transform of the coefficients first.

Synthesis of complex Gaussian signals may also be effected in the same way. The sequence of the given signal, $\hat{x}_i(n)$, then consists of a real and an imaginary part. Correspondingly the coefficients $a_i(n)$ will have a real and an imaginary part, and for real noise v there will be obtained a complex synthesized signal $\bar{x}(n)$. If complex noise is employed, the correlation properties of $\bar{x}(n)$ will more approximate those of a Doppler signal.

Figure 16:
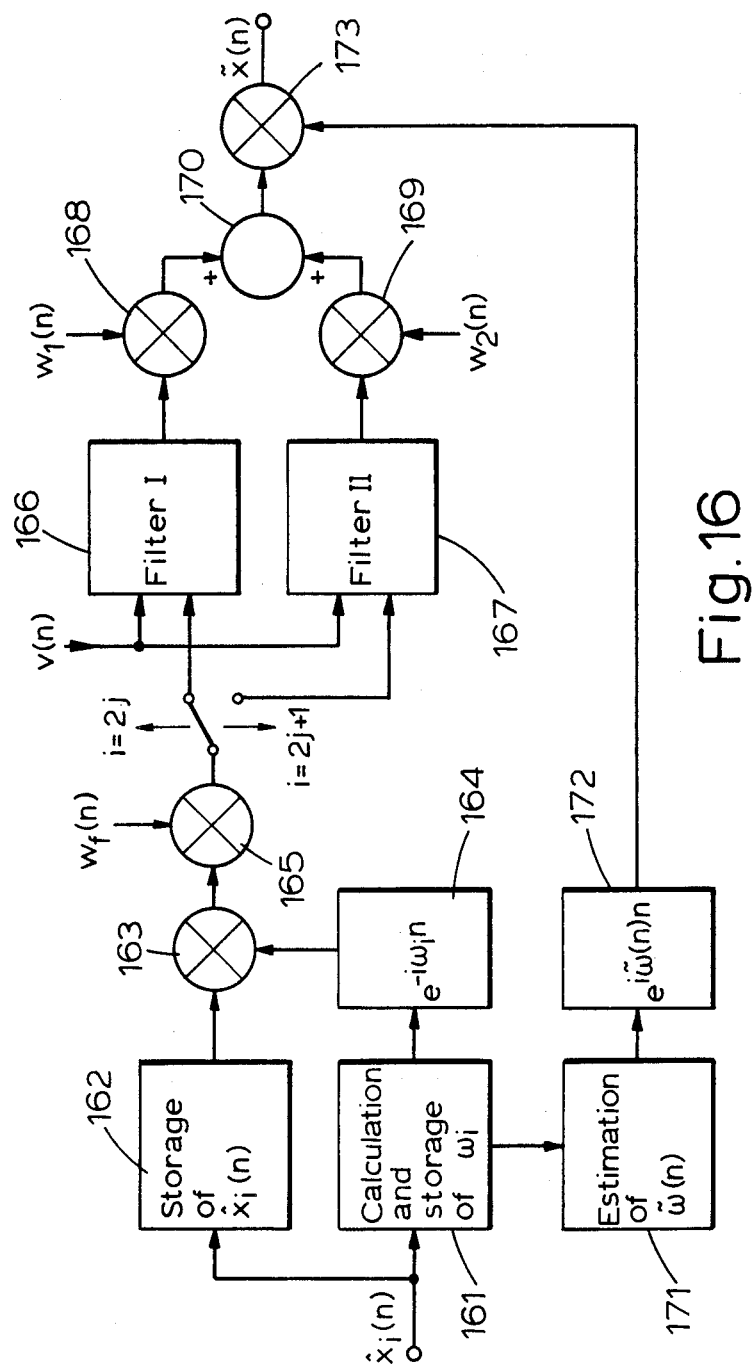
FIG. 16 is a block diagram of a synthesizer for a non-stationary complex signal.

A synthesizer for a non-stationary complex signal is shown in FIG. 16. Segments of the original complex Gaussian signal $\hat{x}_i(n)$ are existing as shown in FIG. 13. The synthesizer is essentially of the same type as the one shown in FIG. 14 for stationary signals, but here the filter coefficients will be time variable. The time variation of the coefficients must be calculated on the basis of several segments of $\hat{x}_i(n)$. This may be done in several ways and FIG. 16 illustrates a method which is applicable with ultrasonic Doppler signals from blood. It is characteristic to such signals that the bandwidth varies comparatively slowly, whereas the maximum frequency is more quickly changed.

For each segment $\hat{x}_i(n)$ there is calculated a characteristic spectral parameter $\omega_i$ in block 161, whereas the segment is stored in block 162. $\omega_i$ may for example be the maximum, the mean or the root mean square of the angular frequency shift. Since the bandwidth of the signal varies slowly, the difference between the maximum and the mean angular frequency shift will vary slowly. Both of these may therefore be employed with the same result, except when in the Doppler signal there are found remainders of signals from tissue in movement. In such a case the maximum angular frequency shift is preferable, because this will be little influenced by the signal from tissue.

The stored segment $\hat{x}_i(n)$ is then multiplied in block 163 with $e^{-i\omega in}$ which is generated in block 164. Thereby the spectrum of $\hat{x}_i(n)$ is moved down to a place around zero frequency (in the following designated the base band), and the change of the short time spectrum given by $\omega_i$ is removed. The complex multiplication may be carried out as in FIG. 17. The result is then multiplied by a window function $w_f(n)$ in block 165, in the same way as in FIG. 15. This forms filter coefficients for a synthesis of a signal which appears in the base band, in the same way as shown in FIG. 14.

FIG. 16 illustrates two filters 166 and 167 for synthesis of the signal in the base band. The coefficients are loaded into the respective filters for every second segment of the original signal. The output of the filters are weighted with weighting functions at 168 and 169 as illustrated in FIG. 18. This involves that the contribution after the summation from the pair of filters 166 and 167 will be zero when the change of coefficients in the filter concerned, takes place. Because of the gradual change of the window function there will be a smooth transition from the situation when the synthesized signal is given by the coefficients from one segment until it is given by the coefficients relating to the following segment. In FIG. 18 there are shown windows with linearly increasing edges, but there may be utilized other windows, for example a Hamming window or the like. The windows must be equal to zero when reading-in of coefficients in the filter concerned, takes place. This time, however, may be made very short (1–5 us).

On the basis of the characteristic angular frequencies $\bar{\omega}_i$ for several segments of the original signal, there is estimated a continuously variable angular frequency $\omega(n)$ in block 171 in FIG. 16. The signal in the base band after block 170 is then multiplied in block 172 by $e^{i\bar{\omega}(n)n}$ generated in block 172. Thereby the spectrum is moved from the base band to the re ion concerned.

A separate method for estimating $\bar{\omega}(n)$ is based upon linear interpolation between $\omega_i$ and $\omega_{i+1}$. This may also be formed by filtering of a number of values of $\omega_i$, since the change of the characteristic angular frequency is band limited.

When forming $\bar{\omega}(n)$ by linear interpolation between $\omega_i$ and $\omega_{i+1}$ the reading-in of the coefficients into the filters 166 and 167 must be delayed so that $\omega_{i+1}$ is present when the coefficients from $x_i(n)$ are loaded. This results in a delay between teh synthesized signal and the original signal, and the field of application determines whether or not this may be tolerated.

A simplified estimator may also employ only one filter instead of two filters as in FIG. 16. A proposal for a weighting function in this case, is shown in FIG. 19.

B. Spectral analysis

Figure 20:
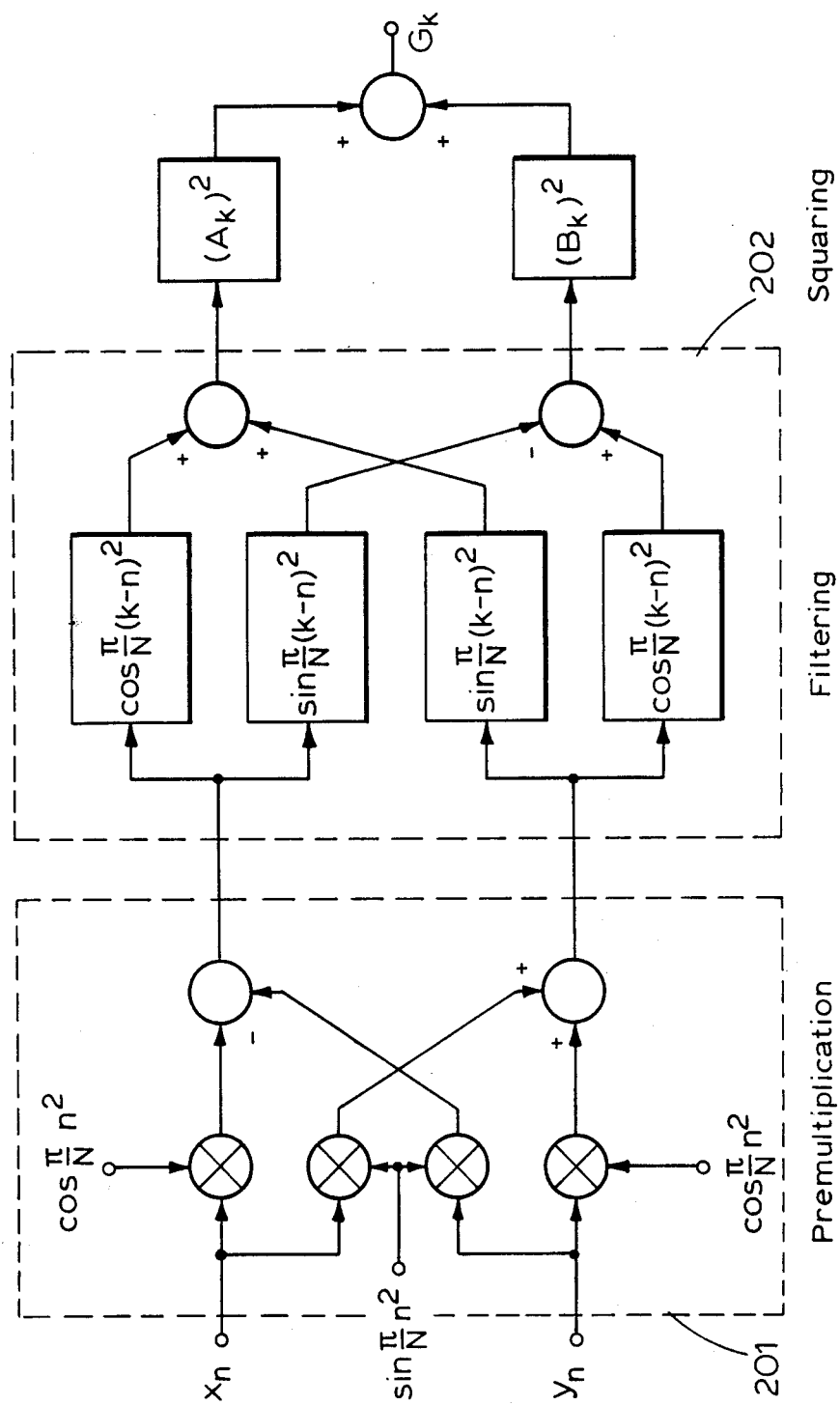
FIG. 20 shows a simplified diagram for the calculation of the power spectrum of the Doppler signal at one depth, by means of the Chirp-z-transform.

Considering again FIG. 8 it appears that the synthesizer 84 is followed by an analyzer 85 for the spectrum analysis of the signal. There is calculated a full power spectrum of the Doppler signal for each depth. For this purpose the Chirp-z-algorithm is used, but also other algorithms, for example the FFT-algorithm may also be used. The Chirp-z-algorithm is described for one depth in the block diagram of FIG. 20. It consists of a premultiplication part 201 and filtering part 202. The filtering is effected by transversal filters which are commercially available for the 64 point and 256 point complex transform AE1 Å. The power spectrum is then formed as $$G_k=|A_k|^2+|B_k|^2 \qquad (16)$$

in which k is the number of the spectrum line.

For most practical purposes the following could be equally well used $$G_k=|A_k|+|B_k| \qquad (17)$$

The employment of the Chirp-z-algorithm for calculating the power spectrum at several depths, may be done in various ways of which two shall be described here.

Figure 21:
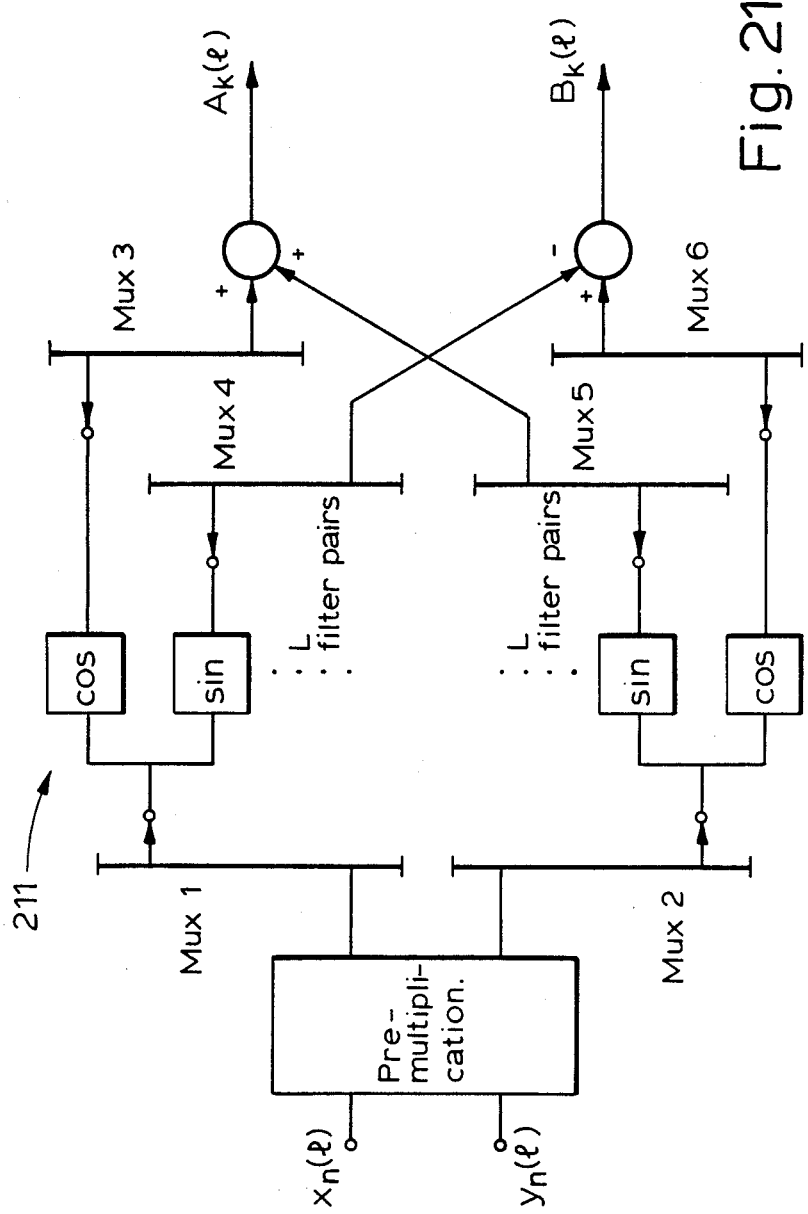
FIG. 21 shows a first example of a diagram for the calculation of the power spectrum for several depths, by means of the Chirp-z-transform.

The first alternative is shown in FIG. 21. The samples of the quadrature components $x_n(l)$ and $y_n(l)$ are fed into a premultiplier 201 as described in FIG. 20. $l=1,\ldots,L$ indicates the depth number and n designates the number of the transmitted pulse. The number of frequency points in the analyzer is N. The same units in the multiplier process all the depths as the signal is received (serial signal processing), and sin $\pi/N$ n, cos $\pi/N$ n change their value at each transmitted pulse. After premultiplication each depth is coupled to separate filter units 211 by the multiplexers Mux 1 and Mux 2. After the filter units the signal from all depths are coupled together in a serial form with the multiplexers Mux 3–Mux 6

Figure 22:
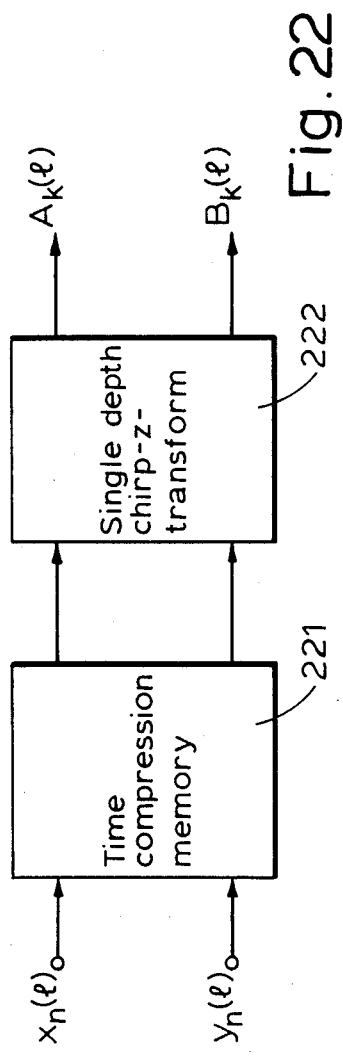
FIG. 22 shows another example of diagram for the calculation of the power spectrum for several depths, by means of the Chirp-z-transform.

The other method is shown in FIG. 22. The quadrature component samples $x_n$ (l) and $y_n$ (l) are digitized and read into a digital memory 221. Time samples of the signal from each depth is quickly read out in sequence and is analyzed by a single depth Chirp-z-transform 222 as described in FIG. 20. In this way there will be obtained a complete serial analysis of the signal. A fast FFT processor may be used instead of the Chirp-z-algorithm.

E. Determination of the maximum and the average Doppler shift

Figure 23:
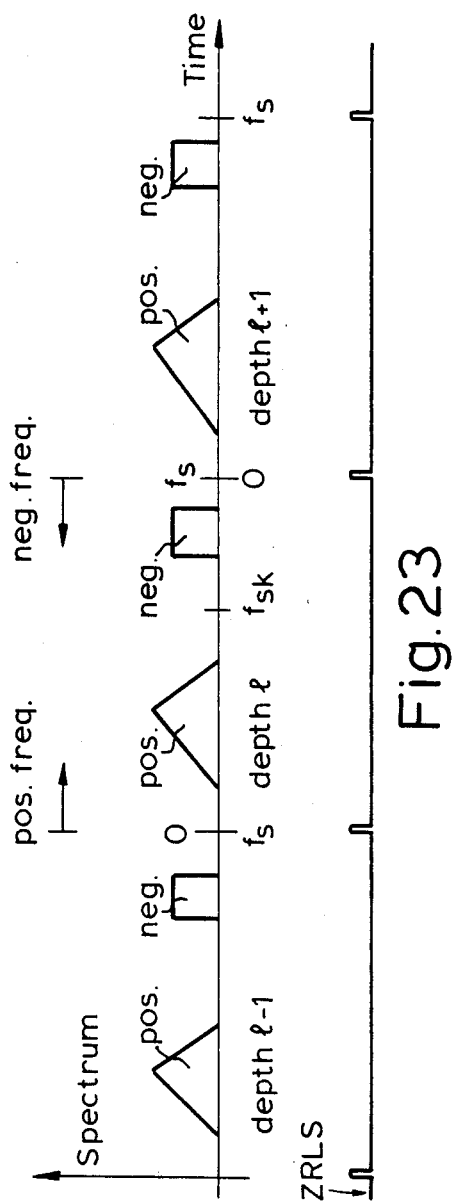
FIG. 23 shows the presentation of spectra for successive depths, from the analyzer in FIG. 8.

Finally, according to FIG. 8 there is carried out a determination of the maximum and the average Doppler shift (frequency) in the block which is designated frequency parameter unit 86. The spectral analyzer 85 is considered to present the spectrum for the various depths serially in time as shown in principle in FIG. 23. The signal ZRLS (zero line sync) is short pulses which indicate the zero line for each depth and also the separation between the depths. The pulse repetition frequency of the Doppler measurement is $f_s$. Positive Doppler shift for each depth goes from 0 and upwards, whereas negative Doppler shift goes from $f_s$ and downwards as indicated in FIG. 23 at depth 1.

$$f_{sk} = \tfrac{1}{2}(f_p + f_n) \tag{20}$$

There will then be positive frequencies from 0 to $f_{sk}$ and negative frequencies from $f_s$ to $f_{sk}$. This may be utilized for organizing the display of the spectrum so that positive Doppler shifts are displayed on the positive side of the zero line whereas negative Doppler shifts are shown on the negative side of the zero line. Thus, positive Doppler shifts can be detected up to L2 and, correspondingly, negative Doppler shifts down to U1.

Figure 26:
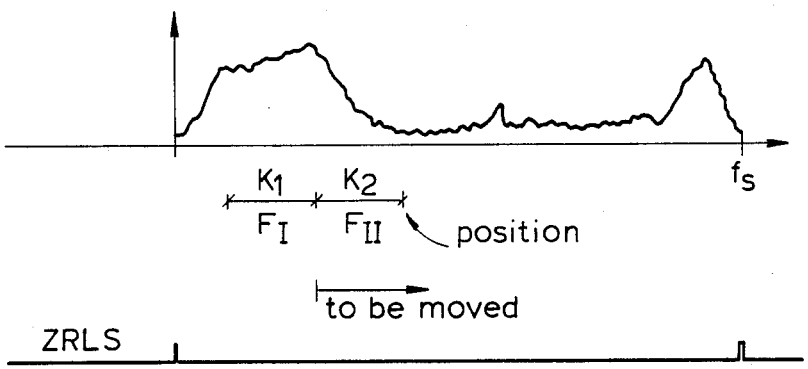
FIG. 26 illustrates the use of frequency windows for determining edges in the spectrum of FIG. 25.
Figure 27:
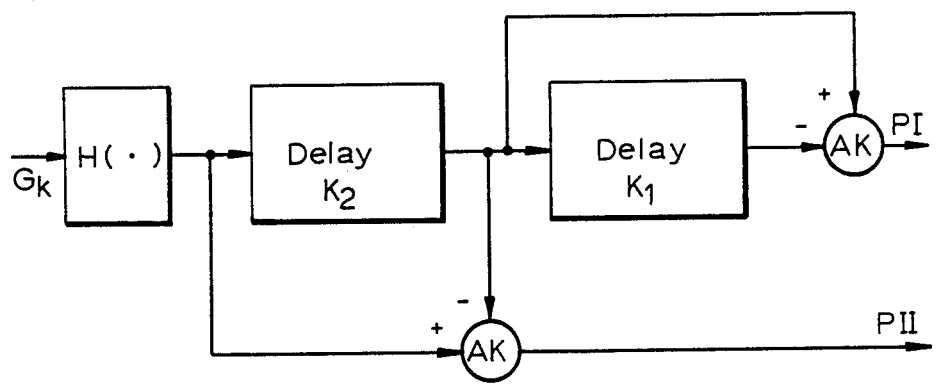
FIG. 27 shows a circuit arrangement for calculating of the sums PI and PII for two frequency windows.
Figure 28:
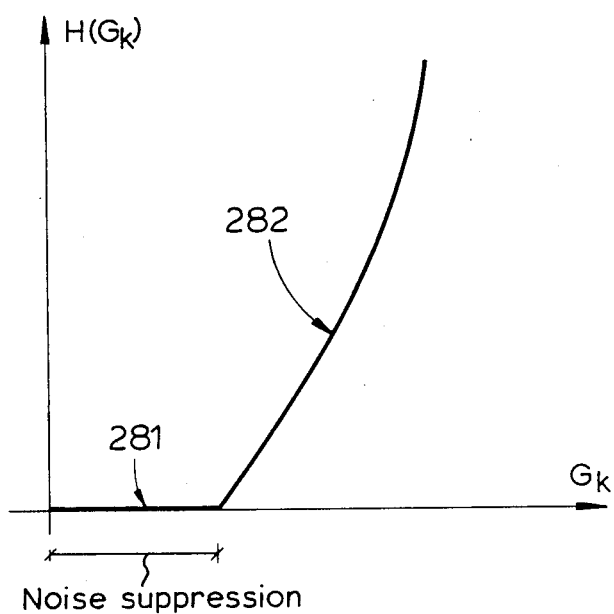
FIG. 28 shows a typical form of a non-linear function which is included in the calculation according to FIG. 27, FIGS. 29a and b illustrate the determination of the lower and the upper edge respectively, of power spectra, FIGS. 30a and b show the readout of short time spectra from an anlyzer for determining edges.

For determining the edges there may be employed two adjacent frequency windows FI and FII as shown in FIG. 26. In the figure these windows have been positioned close to each other, but they may also have a certain spacing, or possibly may overlap each other. The power spectrum is summed over these windows so that one obtains $$PI(K) = \sum_{FI} H(G_k) \qquad PII(K) = \sum_{FII}^{PI_\Sigma} H(G_k) \tag{21}$$

in which K is the number of the spectral line at the right end of FII. H( ) is a non-linear function which may be shaped so as to improve the edge detection. A typical shape of H ( ) is shown in FIG. 28. The curve consists of a first dead band 281 for suppressing the noise and then there is established a suitable shape 282 for enhancing edges. In the case of a continuous spectrum the sums must be replaced by integrals.

The windows are moved from zero towards $f_s$ so that the point of separation moves from 0 to $f_s$. At the same time it is detected when the ratio $$\frac{PI(K)}{PII(K)} \tag{22}$$

It is desirable to extract the maximum Doppler shift corresponding to the maximum velocity in the sample volume, since this gives interesting clinical information. In the following it is described how this may be done from a spectrum formed on the basis of so short segments of the signal (for example 3 ms) that the blood flow is substantially stationary during this time (in the following designated short time spectrum).

Figure 24:
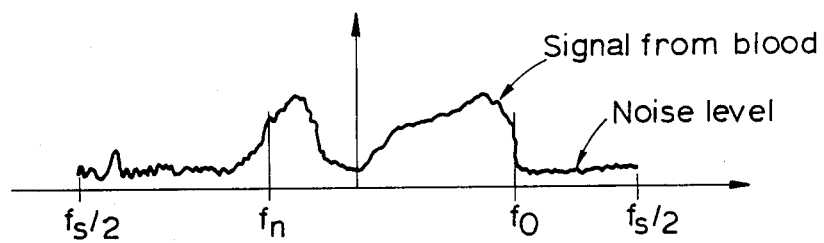
FIG. 24 shows a typical short time spectrum of the Doppler signal from a blood flow.

A typical short time spectrum for a directive Doppler signal from a single depth is shown in FIG. 24. The spectrum consists of a signal from blood and noise with a relatively flat level. There are both positive signal frequencies (velocities towards the transducer) and negative signal frequencies (velocities from the transducer). Since the spectrum is taken over a short time, it will contain random variations about a mean value which is the power spectrum of the signal.

Figure 25:
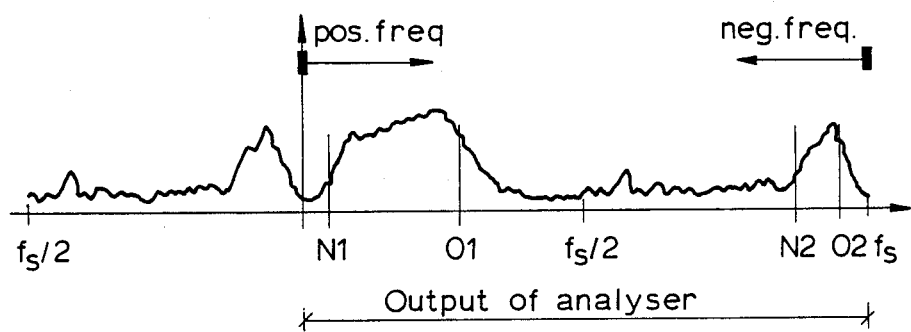
FIG. 25 shows an example of the frequency spectrum of a sampled Doppler signal corresponding to the signal in FIG. 23.

Modern frequency analyzers based upon the FFT (Fast Fourier Transform), or the Chirp-z-transform, operates with samples of the signal. In FIG. 24 $f_s$ is the sampling frequency of the analyzer. The output from the analyzer 85 (FIG. 8) is a set of discrete spectral lines being numbered by k. In order to simplify the figures, the spectra are drawn continuously as an interpolation between the descrete spectral lines. In pulsed Doppler measurements $f_s$ may with advantage be chosen equal to the pulse frequency of the Doppler measurement. In such a sampled system the spectrum will be repeated periodically around multiples of $f_s$ (positive and negative). For the present purpose it is an advantage to employ the zone from 0 to $f_s$ as shown in FIG. 25. The analyzer provides discrete frequency samples $G_k$ from 0 to $f_s$ as a function of time. Positive frequencies go from 0 and upwards, whereas negative frequencies go form $f_s$ and downwards.

If the positive and negative frequencies are too large, they will become intermixed. The common requirement to sampled systems in order to avoid this is $$|f_{max}| < f_s/2 \tag{18}$$

where $f_{max}$ is the maximum Doppler shift present. In pulsed Doppler systems there will only be present samples of the Doppler signal at frequency $f_s$ and equation (18) therefore gives an upper limit of $f_{max}$ which is usually obtained with pulsed Doppler.

However, it is seen from FIG. 25 that by directive spectrum analysis of the Doppler signal, the requirement may be somewhat less strict, such as $$f_u - f_l < f_s \tag{19}$$

in which $f_u$ is the maximum upper Doppler shift, whereas $f_l$ is the maximum lower Doppler shift as shown in FIG. 24. If for example there are only positive frequencies, there may be measured Doppler shifts up to $f_s$ and correspondingly one can measure Doppler shifts down to $-f_s$ when only negative frequencies are present. If the velocities are followed from low values as they increases and equation (19) is satisfied, there is in fact no limit to the magnitude of the velocity which can be measured. Since frequency components which pass $f_s$ reappear at 0, one can keep a record of how many times $f_s$ is passed provided equation (19) is satisfied.

By means of the method described here one may be able to automatically detect edges in the spectrum and thereby automatically determine the point of transition between positive and negative Doppler shifts. Thus, it will be equation (19) which is valid for maximum permitted Doppler shift instead of equation (18).

In the spectrum as shown in FIG. 25 there are two lower edges L1 and L2, and two upper edges U1 and U2. Assume that the lower range from L1 to U1 has been detected as positive Doppler shifts, whereas the upper range from L2 to U2 has been detected as negative Doppler shifts. There may then be defined a maximum positive edge $f_p = U1$ and a maximum negative edge $f_n = L2$. A frequency of separation between positive and negative frequencies is then chosen between these, for example as is changed from $<\alpha$ to $>\alpha$. This gives the lower edges in the spectrum. $\alpha$ is a constant $<1$ which is determined from the lowest signal-to-noise ratio where edges are to be detected. The edge of interest is then determined as $$L = K - (K_2 + D) \quad (23)$$

as illustrated in FIG. 29. D has been introduced because a short time spectrum has always a limited edge slope and one must allow some power in PI in order to obtain a safe detection of the edge. One choose D so that L is located at the spectral edge.

Upper edges in the spectrum are found by detecting the location at which the ratio $$\frac{PII(K)}{PI(K)} \quad (24)$$

changes from being $>\alpha$ to $<\alpha$.

The edge of interest is then determinded as $$U = K - (K_2 - D) \quad (25)$$

as indicated in FIG. 29, in which D has the same function as in equation (23).

Figure 32A:
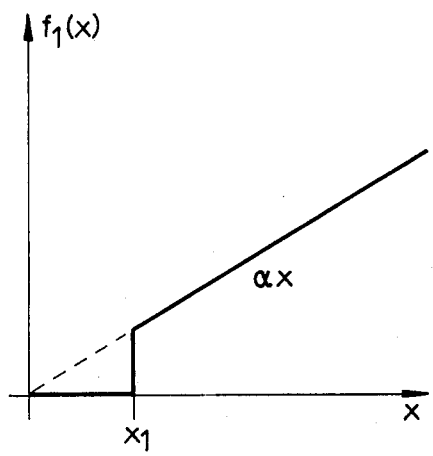
Figure 32B:
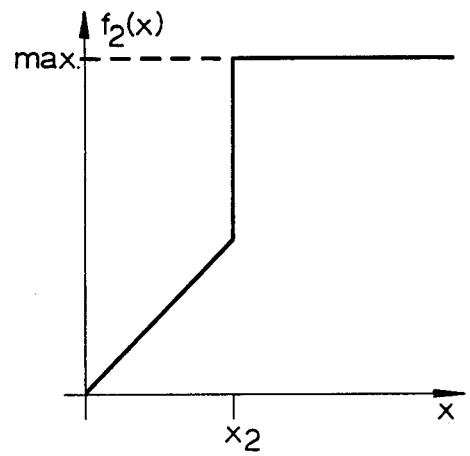

Additional noise suppression may take place by making PI and PII undergo monotinical mappings $f_1(\cdot)$ and $f_2(\cdot)$ whereby for example $f_1(x)$ is essentially equal to x, but may have a dead band for $x < x_1$ and $f_2(x)$ is essentially equal to x, but may be set to be a high fixed value for $x > x_2$ as indicated in FIG. 32. This latter precaution contributes to avoiding detection of local edges in the short time spectrum due to random variations because of the short time segment of the signal which has been taken as a basis for calculation of the spectrum.

The lower edges are determined at the point where the ratio $$\frac{f_2(PI)}{f_1(PII)} \quad (26)$$

changes from being $>1$ to $<1$.

In order that the middle point between the frequency windows may be moved over the whole range from 0 to $f_s$, there must be inserted $K_2$ zeros at the end of the spectrum after $f_s$. It is therefore necessary to have a space of at least $K_2$ spectral lines between the presentation of subsequent spectra as shown in FIG. 30. The signal ZRLS (zero line sync) are short pulses which indicate the zero line for each depth.

Figure 31:
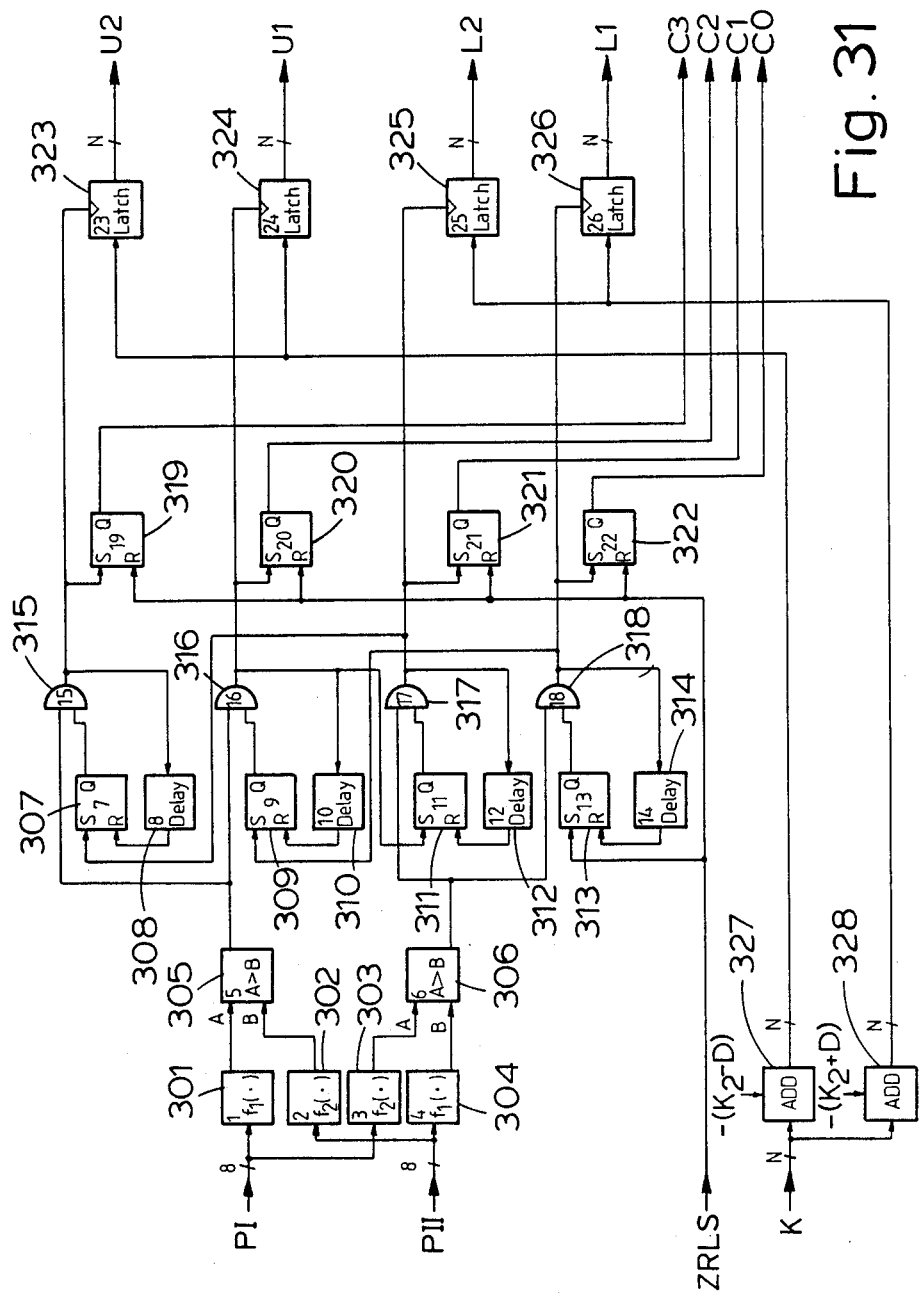
FIG. 31 is a block diagram of a system for determining the lower and the upper edges according to FIG. 29, FIGS. 32a and b show examples of non-linear functions which are included in the system of FIG. 31, FIGS. 33a, b and c represent various situations which may occur as far as spectra are concerned.

FIG. 31 shows an electronic system which determines the edges in the spectrum. This is one example and the method may for example be programmed in a microprocessor. The discrete spectral lines from 0 to $f_s$ having $K_2$ zeros added thereto, are described by a binary number K. This gives the address of the spectral lines in the device shown in FIG. 27 and thereby the address to the right-hand point in window FII (FIG. 26). The upper edges are found by sampling $(K - (K_2 - D))$ when the ratio according to equation (26) passes through 1 as described above. In the same way the lower edge is determined by sampling $K - (K_2 + D)$ when the ratio according to equation (25) passes through 1 in accordance with equations (22) and (24). The addresses are sampled by the blocks LATCH 323–26 and the address change takes place in blocks 327–28, FIG. 31.

PI and PII are continuously clocked into ROM units 301–304, FIG. 31. These represent non-linear functions $f_1$ and $f_2$ as illustrated in FIG. 32. The comparator output in block 305 will go high when the ratio according to equation (26) changes from being $>1$ to being $<1$. The output therefore will go high at the detection of an upper edge. Correspondingly the comparator output in block 306 will go high when the ratio according to equation (25) changes from being $<1$ to being $>1$.

Figure 33A:
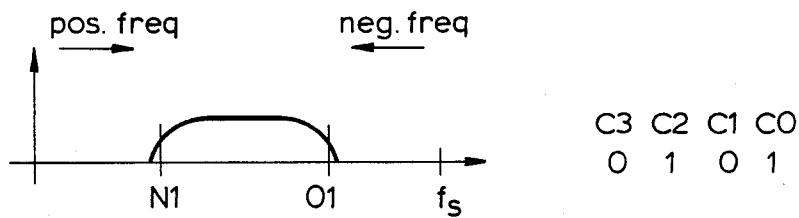
Figure 33B:
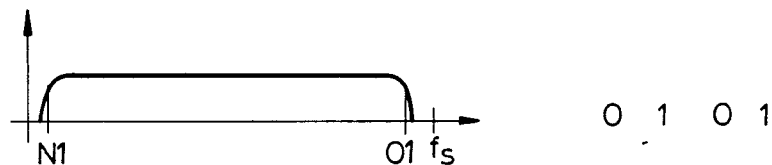
Figure 33C:
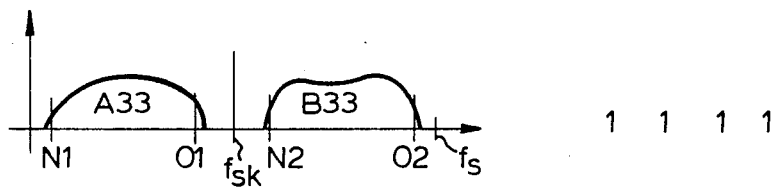

Normally there will be three different situations as shown in FIG. 33. Consider first the situation of FIG. 33c in which there are two lower (L1 and L2) and two upper (U1 and U2) edges. When starting to analyze a spectrum there will appear a pulse in ZRLS as shown in FIG. 30. This sets the flip-flop 313 (FIG. 31) which opens for detection of the first lower edge, and when comparator 306 goes high, the signal is conveyed through 318 to LATCH 326 which samples $K - (K_2 + D)$. Thereby the lower edge L1 is obtained. At the same time flip-flop 322 is set so that control signal C0 goes high and indicates that the first lower edge has been sampled. Through a short delay given by block 314 the flop-flop 313 is reset and this prevents new values from being sampled into LATCH 326. The sampling pulse from 318 also sets flip-flop 309 which thereby opens for detection of the first upper edge U1. When the output of comparator 305 goes high, $K - (K_2 - D)$ is sampled in LATCH 324 and this gives U1. C2 goes high by setting of flip-flop 320 and this indicates that U1 has been detected. After a short delay in block 310 flip-flop 309 is reset and blocks for additional sampling in LATCH 324. The pulse from 316 also sets 311 which opens for detection of another lower edge L2 in block 325. When L2 is detected flip-flop 307 is set and opens for detection of the next upper edge U2.

When all four edges have been detected, all bits in the control word C0 . . . C3 will be high as shown in FIG. 33c. If there are only two edges as in FIG. 33a, b, only C0 and C2 will be high, whereas C1 and C3 will be low. The control word indicates which situation is present and also indicates an error situation if other values are represented than what is shown in FIG. 33. Flip-flops 307, 309, 311, 313 are used for opening and blocking for detection of the edges of interest so that L1, U1, L2, U2 follow in sequence and so that only the first detection of an edge is valid. This has been done in order to reduce the unfavourable effects of local edges in the short time spectrum. After the edge detection it is necessary to sort out which edges give maximum positive and maximum negative frequency, respectively. Because of the periodicity of the spectrum, increasing positive frequencies for example, which pass $f_s$ will reappear above 0 and correspondingly will decreasing negative frequencies which pass 0 reappear below $f_s$. By counting how many times the spectrum passes 0 or $f_s$, it is possible to follow the maximum Doppler shift without limitation as long as equation (19) is satisfied. Because of the periodicity, 0 and $f_s$ are equivalent frequencies, and instead of organizing the spectrum for 0 to $f_s$ as above, the spectrum may without limitations be organized from $-\Delta$ to $-\Delta+f_s$, whereby $\Delta$ may be freely chosen. In order to simplify the description one chooses $\Delta=0$ without restricting the general validity.

The spectrum obtained may have three typical forms as indicated in FIG. 33. It is characteristic to FIG. 33a and b that there are only two edges, whereas in FIG. 33c four edges are found. In FIG. 33b the spectrum covers the whole band except for a range around 0 and $f_s$ which is removed by the high-pass filter. This indicates that equation (19) is not satisfied and that fequency ambiguity (aliasing) is present. In the following these three situations shall be systematically discussed:

Situation I

The spectrum in FIG. 33a may either have positive Doppler shift from 0 to U1 or negative Doppler shift from $f_s$ to L1. It must then be decided first whether this is positive or negative Doppler shifts. This may for example be done by following the variation of the velocity during the cardiac cycle, from low Doppler shifts to higher and to take advantage of the fact that the velocity is continuous with time. With the multi-gated Doppler measurement treated here, the velocity may be observed as a function of depth (from low Doppler shift) and one may take advantage of the fact that the velocity is continuous as a function of depth. If the frequencies are positive, there will exist a positive maximum frequency $$f_{+max} = U1 + m f_s \tag{27}$$

in which m is a positive integer which indicates how many times the spectrum has passed by $f_s$. Note that when the spectrum passes by $f_s$ upwardly, it will reappear around 0 because of the periodicity of the spectrum analysis. By following the spectrum changes over time, there is as mentioned above, no limit to the magnitude of the Doppler shifts which may be measured by pulsed Doppler measurement as long as equation (19) is satisfied and the Doppler spectrum is moving by less than $f_s$ between subsequent spectra. Note that $f_s$ is here the pulse repetition frequency of the transmitted pulses as well as the band-width of the spectrum analyzer.

When the spectrum passes $f_s$, parts thereof will reappear above 0 vhereas another part will be found just below $f_s$. Because of the high-pass filter of the Doppler instrument there is removed a band around 0 and $f_s$, and the spectrum will then have four edges. This situation is described more closely below.

When $f_{+max}$ has obtained its maximum value and starts to decrease, m must be decremented each time the spectrum passes by 0. There may also occur a situation in which equation (19) is satisfied only during a portion of the cardiac cycle. When the condition according to the equation is not fulfilled, it may for example be provided for holding the value of m until the band-width of the spectrum again satisfies equation (19). In order to eliminate error situations in the counting of m, one sets m=0 if the Doppler signal disappears.

It may be an advantage to define a maximum positive edge $$f_p = U1 \tag{28}$$

and a minimum negative edge $$f_n = f_s \tag{29}$$

The point of separation between positive and negative frequencies is then located between these, for example by equation (20).

At negative Doppler shifts the following shall apply:

$$f_{-max} = L1 - f_s + m f_s \tag{30}$$

in which m is a negative integer which indicates the number of times the spectrum has passed by 0 downwards. In a corresponding way a maximum positive edge is set at $$f_p = 0 \tag{31}$$

and minimum negative edge $$f_n = L1 \tag{32}$$

$f_{sk}$ is then defined between $f_p$ and $f_n$ as above.

Decrementing of $|m|$ must be effected when $|f_{-max}|$ commences to decrease and m is set to zero the Doppler signal disappears, corresponding to what applies for positive Doppler shifts.

Situation II

In the situation of FIG. 33 edges L1 and U1 are located at the cut-off frequency of the Doppler instrument high-pass filter. In this situation there exists a frequency ambiguity which it is not possible to correct for. By the control work 0101 one must therefore check the distance from 0 to L1 and U1 to $f_s$ so as to decide whether or not aliasing is present. If it is not, the first situation is present, and it must be decided whether there is a positive or a negative Doppler shift and then use equation (27) or equation (30). If there is aliasing, it is not possible to determine a maximum frequency. There should be delivered a separate message stating that situation II exists. This may be done for example by inserting a certain color code in the two-dimensional Doppler image at the points concerned.

Situation III

The situation of FIG. 33c may theoretically occur in three ways (i) A33 represents moderate positive and B33 moderate negative Doppler shifts.

(ii) A33 represents large negative and B33 large positive Doppler shifts. In practice there will not occur large positive and large negative Doppler shifts with separate spectra simultaneously. Therefore, this case may be excluded as theoretical.

(iii) If one has the situation of FIG. 33a and the velocity increases such that the maximum frequency passes $f_s$ or 0, a situation as illustrated in FIG. 33c will occur.

The Doppler instrument high-pass filter will remove frequencies around 0 and $f_s$ so that four edges will result.

In situation (i) one will have $$f_{+max} = U1$$

$$f_{-max} = L2 - f_s \quad (33)$$

$f_{sk}$ is then defined as in equation (18), in which $f_p = U1$ and $f_n = L2$.

Situation (ii) is not of interest in practice. In order to decide whether situation (iii) is present, one may follow the development of situation 33a as a function of time from low velocities. With the multi-gated instrument concerned the development may be followed as a function of depth from low velocities. If at one time (depth) there is present a spectrum of type 33a and in the next a type 33c spectrum, it can be concluded that situation (iii) is present. Moreover, situation (iii) is present as long as the spectrum is passing by m $f_s$ so that spectra of the shape shown in FIG. 33c are obtained. When the spectrum has passed by $f_s$, there is again situation I. At positive Doppler shifts the following is then set $$f_{+max} = mf_s + U1$$

$$f_p = U1 \; f_n = L2 \quad (34)$$

m is an iteger which indicates how many times U1 has passed by $f_s$.

With negative Doppler shift the following applies $$f_{-max} = L2 - f_s + mf_s$$

$$f_p = U1 \; f_n = 2 \quad (35)$$

in which m is a negative integer which indicates how many times L1 has passed by 0 downwards. As in situation I it is necessary to decrement m when the Doppler shift starts to decrease, and is reset to 0 when the Doppler signal disappears.

From $f_{+max}$ and $f_{-max}$ it may be of interest to present the one which has the highest absolute value $$f_{max} = \begin{cases} f_{+max} & f_{+max} \geq |f_{-max}| \\ f_{-max} & \text{otherwise} \end{cases} \quad (36)$$

By employing the m which is determined above, there may be corrected for the frequency ambiguity in the display of the spectrum. For example in situatin I this may take place by adding $mf_s$ to the requency coordinate both for positive and negative frequencies. In situation III—iii) one may with positive frequencies add $mf_s$ to the frequency coordinate for $f_k < f_{sk}$ and $(m-1)f_s$ for $f_k > f_{sk}$ and correspondingly at negative frequencies add $m \; f_s$ for $f_k > f_{sk}$ and $(m+1)f_s$ for $f_k < f_{sk}$.

Correction for the frequency ambiguity of the average Doppler shift f may be effected by $$f = mf_s + \frac{\sum\limits_{0}^{f_{sk}} f_k G_k + \sum\limits_{f_{sk}}^{f_s} (f_k - f_s) G_k}{\sum\limits_{0}^{f_s} G_k} \quad (37)$$

It is also possible to present the average Doppler shift for positive and negative frequencies separately.

Situation I—positive Doppler shifts $$f_+ = mf_s + \frac{\sum\limits_{0}^{f_{sk}} f_k G_k}{\sum\limits_{0}^{f_{sk}} G_k} = f \quad (38)$$

$$f_- = 0$$

Situation I—negative Doppler shifts $$f_+ = 0 \quad (39)$$

$$f_- = mf_s + \frac{\sum\limits_{f_{sk}}^{f_s} (f_k - f_s) G_k}{\sum\limits_{f_{sk}}^{f_s} G_k} = f$$

Situation II

Because of aliasing (frequency ambiguity) the average and maximum Doppler shifts are unknown and a message in this regard is given.

Situation III—(i)

$$f_+ = \frac{\sum\limits_{0}^{f_{sk}} f_k G_k}{\sum\limits_{0}^{f_{sk}} G_k} \quad (40)$$

$$f_- = \frac{\sum\limits_{f_{sk}}^{f_s} (f_k - f_s) G_k}{\sum\limits_{f_{sk}}^{f_s} G_k}$$

Situation III—(iii)—positive Doppler shifts $$f_+ = mf_s + \frac{\sum\limits_{0}^{f_{sk}} f_k G_k + \sum\limits_{f_{sk}}^{f_s} (f_k - f_s) G_k}{\sum\limits_{0}^{f_s} G_k} = f \quad (41)$$

$$f_- = 0$$

Situation III—(iii)—negative Doppler shifts $$f_+ = 0 \quad (42)$$

$$f_- = mf_s + \frac{\sum\limits_{0}^{f_{sk}} f_k G_k + \sum\limits_{f_{sk}}^{f_s} (f_k - f_s) G_k}{\sum\limits_{0}^{f_s} G_k} = f$$

When the signal-to noise ratio is low it may be difficult to determine $f_{sk}$. For calculating f one may then put $f_{sk} = f_s/2$.

Figure 34:
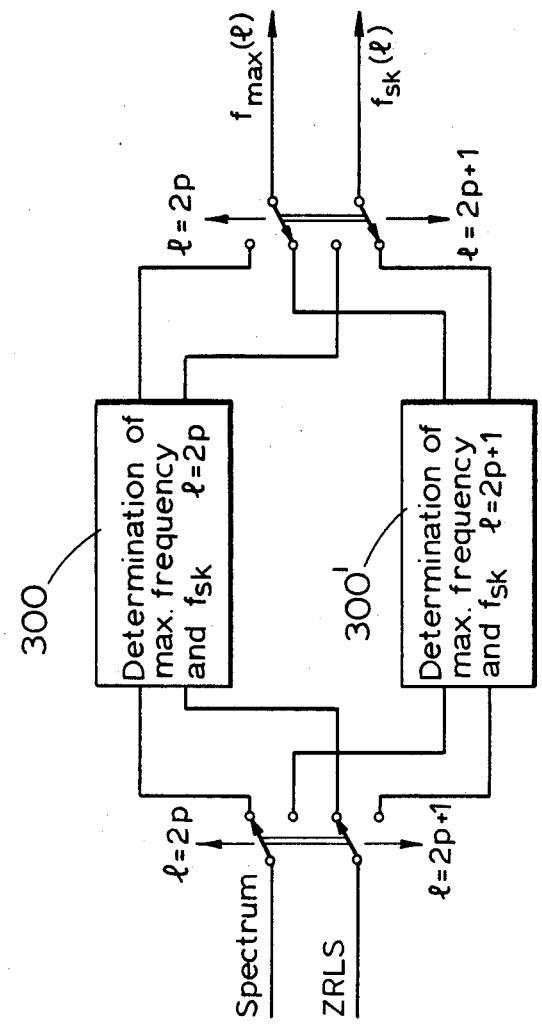
FIG. 34 shows the employment of two units according to FIG. 31 for determining maximum Doppler shift as function of depth.
Figure 35:
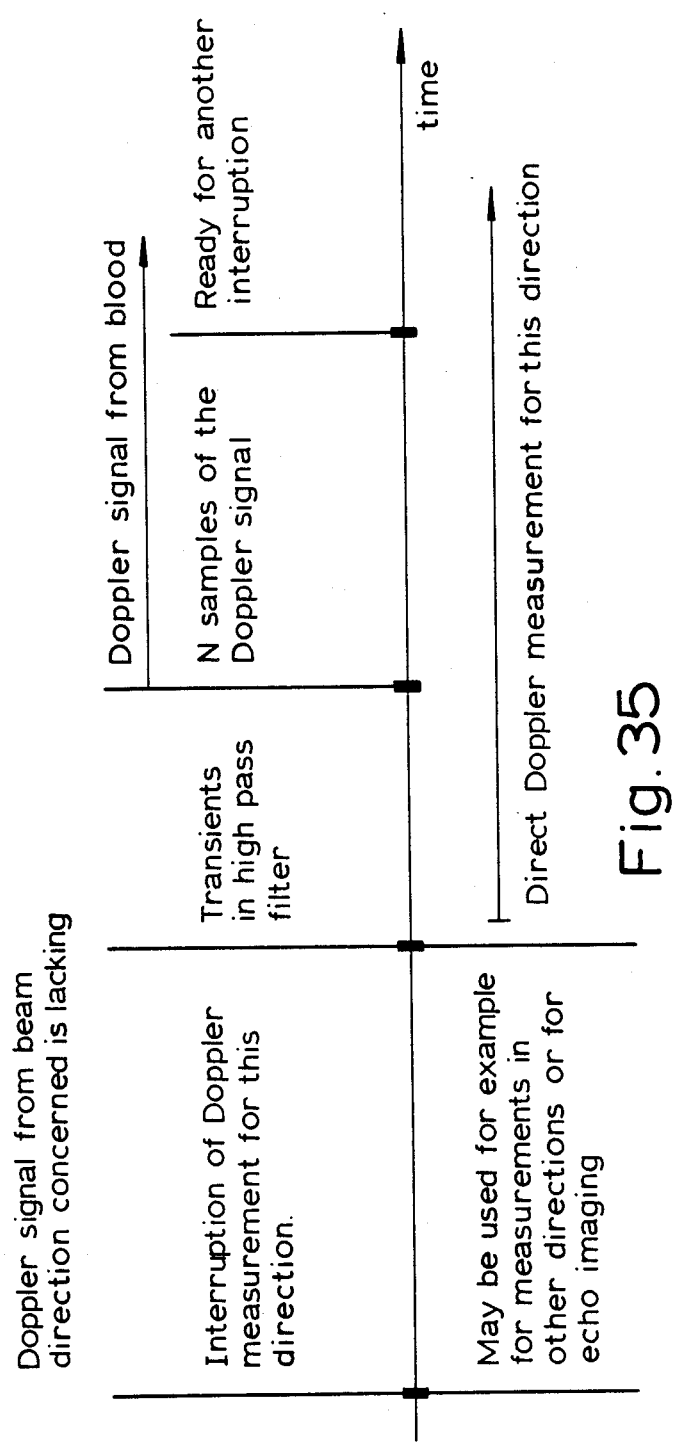
FIG. 35 is an example of time sharing when the Doppler measurement from one sample volume is interrupted to do Doppler measurements in other directions or to form an echo amplitude image.

The method employed for determining maximum Doppler shift assumes that there is a dead time between the presentation of each spectrum. In order to obtain this there must be used a parallel analysis as for example indicated in FIG. 34 in which there is employed two units according to FIG. 31. It is of interest to employ single chip microprocessors for carrying out the calculations. The calculation time will then be so long that there must be applied more than two parallel units 300 and 300' as shown. From the units there will be obtained maximum Doppler shift $f_s$ and a separation between positive and negative frequencies $f_{sk}$, as described above. $f_{sk}$ is indicated in FIG. 23 for the depth 1.

F. Spectral interpolation versus Doppler signal synthesis.

The Doppler spectrum together with maximum and average Doppler shift as a function of depth, may be frozen in the display unit during the interupt period. For this reason it is sufficient to take N samples of the Doppler signal for the analysis which is necessary in order to generate a new Doppler spectrum with the desired accuracy. Typical values of N may be 16, 32, 64, 128. After that the system is ready for a new interrupt. For example with the Chirp-z-transform using "Bucket Brigade" devices, it will often be defined by the electronics (hardware) how many samples of the Doppler signal are needed by the spectrum analyzer for calculating a spectrum. Missing signal samples may then be replaced by zeros until there are a sufficient number of values for the analyzer. N may then be chosen freely smaller than the number required by the analyzer.

Normally the interrupts will be made regularly. Thereby one can calculate samples of the Doppler spectrum at certain time intervals. These samples may be used for displaying the development of the Doppler spectrum as a function of time for selected depths, as discussed above. If the interupt intervals become long, the spectra may change much between each sample. It may then be of interest to use an interpolated display of the spectrum between these samples.

As described it is, moreover, useful to present the Doppler signal in an audible manner at selected depths. The interrupts in the Doppler measurement will disturb the audible signal. This may be attended to by replacing the Doppler signal with a substitute signal either during all the time or during portions of the time when the direct original signal is missing.

Since the analyzer part of the instrument only needs N samples of the Doppler signal, the time for direct measurement of the Doppler signal may be made short in relation to the interrupt period, by employing a synthesizer according to FIG. 6. It is then preferable to present the synthetic Doppler signal all the time. The filter coefficients are then calculated on the basis of N Doppler samples between certain time intervals, for example as also described above with respect to one depth. The coefficients may then be allowed to vary as a function of time so that there will be smooth changes in the spectrum of the synthesized signal. This spectrum may then be used as an interpolated version of the sampled Doppler spectrum for display as a function of time for the depths selected.

We claim:

1. Method for generating a multidimensional map of blood velocities in the circulatory system of living species, using the Doppler effect of backscattered ultrasound, the flow map being shown in real time on a display device, with the ability to select small sample volumes in the map where an approximate spectral analysis of the Doppler signal can be shown on a display as a function of time together with the moving flow map in real time to illustrate the time variation of the blood velocities in the sample volumes selected, comprising the steps of:
    (a) transmitting a pulse type ultrasonic beam which is swept in two or more dimensions through a region of the biological structure which is to be investigated;
    (b) sampling the backscattered ultrasonic signal in a plurality of sample volumes along each beam direction of the transmitted ultrasonic pulses;
    (c) determining a velocity parameter of the blood flow for each sample volume and beam direction by means of the Doppler principle;
    (d) assigning a coded presentation on a display screen, displaying said velocity parameters for each sample volume and beam direction as a flow map; synthesizing continuous substrate signals from segments of said backscattered signal from selected sample volumes to produce a continuous representation of the signal from these sample volumes;
    (e) audibly presenting and frequency analyzing said continuous representation to estimate the variation of the blood velocities in said selected sample volumes as a function of time; and
    (f) displaying said frequency analyzed signal on a display.

2. Method according to claim 1, wherein the step of determining, for each sample volume and beam direction the velocity parameter of the blood flow by means of the Doppler principle, comprises determining the maximum velocity of the blood flow in each sample volume.

3. Method according to claim 1, wherein the step of determining, for each sample volume and beam direction the velocity parameter of the blood flow by means of the Doppler principle, comprises determining the average velocity of the blood flow in each sample volume.

4. Method according to claim 1, wherein the step of determining, for each sample volume and beam direction the velocity parameter of the blood flow by means of the Doppler principle, comprises determining the spectral width of the blood flow.

5. Method according to claim 1 wherein the step of determining, for each sample volume and beam direction the velocity parameter of the blood flow by means of the Doppler principle, comprises employing a combination of average velocity of the blood flow and range of the blood velocity distribution within each sample volume.

6. Method according to claim 1, wherein the ultrasonic beam is swept continuously over the region to be investigated.

7. Method according to claim 1, wherein the coded presentation of the velocity parameters takes place in the form of a gray scale.

8. Method according to claim 1, wherein the coded presentation of the velocity parameters takes place in the form of a color scale.

9. Method according to claim 1, wherein the velocity parameter is determined on the basis of a spectral analysis of the signal.

10. The method of claim 1 further comprising the steps of
    (g) combining the imaging of the velocity parameters with an echo amplitude imaging of the biological structure by time-sharing between Doppler measurements and amplitude imaging, whereby information from the echo imaging is displayed on the screen in combination with the velocity parameter images.

11. Apparatus for performing a method for generating a multidimensional map of blood velocities in the circulatory system of living species, using the Doppler effect of backscattered ultrasound, the flow map being shown in real time on a display device, with the ability to select small sample volumes in the map where an approximate spectral analysis of the Doppler signal can be shown on a display as a function of time together with the moving flow map in real time to illustrate the time variation of the blood velocities in the sample volumes selected comprising:
   (a) ultrasonic transmitting means including a transducer for transmitting an ultrasonic signal;
   (b) ultrasonic receiver means for receiving said backscattered ultrasound;
   (c) Doppler processor means coupled to said receiver means for sampling the backscattered signal at a number of sample volumes along a number of beam directions for determining a velocity parameter;
   (d) a diplay means;
   (e) a control means coupled to said Doppler processor means for controlling the Doppler processor means and to the display means so that the velocity parameters from the whole region investigated are displayed in a coded form;
   (f) selecting means for selecting sample volumes in said flow map for display as a function of time;
   (g) synthesizer means for generating substitute signals to provide a continuous representation of the Doppler signal from the selected sample volumes;
   (h) an analyzer means for frequency analyzing said substitute signals and having an output signal which represents an estimate of the variation of the blood velocities in the selected sample volumes as a function of time;
   (i) means for displaying said analyzed signal on one of said display means and another display device.

12. Apparatus according to claim 11, further comprising an echo amplitude processor having circuitry for pulse echo amplitude imaging of the biological structure, said echo processor being controlled by a control signal from said control means for operating in a time-sharing mode with said Doppler processor means to display echo amplitude image information on said display means in combination with the flow map of the velocity parameters.

13. Apparatus according to claim 11 in which the Doppler processor means comprises a high-pass filter for removing backscattered signal components due to tissue structure further including a capacitor bank having a plurality of capacitors; means for electronically switching said capacitors to form a series capacitor of the high-pass filter, each of said plurality of capacitors in the capacitor bank being separately addressable by said switching means for connecting a selected capacitor for each depth point, means for scanning the output of the high-pass filter with a small time delay ($\tau$) with respect to the connection of a capacitor, said frequency analyzer provided after the high-pass filter for determining a frequency spectrum of the backscattered signal in each depth point; and, means for calculating a frequency parameter from said output signal of said frequency analyzer means.

* * * * *